United States Patent [19]

Miller et al.

[11] Patent Number: 4,929,767

[45] Date of Patent: May 29, 1990

[54] TREATMENT OF RHODIUM CATALYSTS

[75] Inventors: David J. Miller, Charleston; David R. Bryant, South Charleston; Ernst Billig, Charleston, all of W. Va.; Bernard L. Shaw, Leeds, England

[73] Assignee: Union Carbide Chemicals and Plastics Company Inc., Danbury, Conn.

[21] Appl. No.: 254,197

[22] Filed: Oct. 6, 1988

Related U.S. Application Data

[63] Continuation-in-part of Ser. No. 231,508, Aug. 12, 1988.

[51] Int. Cl.$^5$ .................... C07C 45/50; C04B 35/00
[52] U.S. Cl. .................... 568/454; 502/150; 502/155; 556/15; 556/12; 568/429; 568/438; 568/492
[58] Field of Search ............ 568/429, 438, 454, 492; 556/15, 22; 502/155, 150

[56] References Cited

U.S. PATENT DOCUMENTS

| 3,527,809 | 9/1970 | Pruett et al. | 568/454 |
|---|---|---|---|
| 3,555,098 | 1/1971 | Olivier et al. | 568/455 |
| 4,013,584 | 3/1977 | Knifton | 252/415 |
| 4,021,463 | 7/1977 | Kummer et al. | 260/429 R |
| 4,041,082 | 8/1977 | Onoda et al. | 568/454 |
| 4,196,096 | 4/1980 | Dawes et al. | 252/414 |
| 4,221,743 | 0/1980 | Halstead et al. | 568/454 |
| 4,242,284 | 12/1980 | Harris | 568/454 |
| 4,248,802 | 2/1981 | Kuntz | 568/454 |
| 4,283,304 | 8/1981 | Bryant et al. | 252/413 |
| 4,292,196 | 9/1981 | Homeier et al. | 252/412 |
| 4,297,239 | 10/1981 | Bryant et al. | 252/412 |
| 4,364,907 | 12/1982 | Barnes | 423/22 |
| 4,374,278 | 2/1983 | Bryant et al. | 568/454 |
| 4,429,161 | 1/1984 | Abatjoglou et al. | 568/14 |
| 4,504,588 | 3/1985 | Gartner et al. | 502/24 |
| 4,537,997 | 9/1985 | Kojima et al. | 568/454 |
| 4,547,595 | 10/1985 | Chang | 568/454 |
| 4,568,653 | 2/1986 | Schwarten | 568/454 |
| 4,605,780 | 8/1986 | Billig et al. | 568/454 |
| 4,613,701 | 8/1986 | Strong et al. | 568/454 |
| 4,633,021 | 12/1986 | Hanes | 568/454 |

FOREIGN PATENT DOCUMENTS

| 51-23212 | 2/1976 | Japan | 568/454 |
|---|---|---|---|
| 58-185534 | 4/1983 | Japan | 568/454 |

Primary Examiner—Werren B. Lone
Attorney, Agent, or Firm—Reynold J. Finnegan

[57] ABSTRACT

A process for treating an organic solution of a partially deactivated solubilized rhodium-tertiary organophosphine complex hydroformylation catalyst with an organic reagent in order to improve the extractability of rhodium therefrom into an aqueous solution containing an ionic organophosphine ligand.

27 Claims, No Drawings

TREATMENT OF RHODIUM CATALYSTS

This application is a Continuation-In-Part of U.S. Patent Application Ser. No. 231,508 filed Aug. 12, 1988.

This invention relates to a process for treating an organic solution containing a partially deactivated rhodium - tertiary non-ionic organophosphine complex catalyst with certain organic reagents to obtain an organic solution of an organic reagent treated solubilized rhodium - tertiary non-ionic organophosphine complex product which contains more rhodium correspondingly capable of being extracted into an aqueous solution containing an ionic organophosphine ligand, than contained in the organic solution starting material before said treatment.

BACKGROUND OF THE INVENTION

Processes using rhodium - tertiary non-ionic organophosphine complexes as homogeneous catalysts are well-known. Included in such processes are the hydrogenation of unsaturated compounds, the carbonylation of methanol to acetic acid, olefin dimerization and oligomerization processes, the hydrocyanation of butadiene to adiponitrile and olefin hydrosilylation reactions. Still other processes are known to those skilled in the art. Oftentimes, recovery of the rhodium from the catalyst solutions used in these process presents a particulary troublesome problem.

Particularly illustrative of these homogeneous catalysis systems is the hydroformylation of olefinic compounds with carbon monoxide and hydrogen to produce aldehyde products in the presence of a rhodium - tertiary organophosphine complex hydroformylation catalyst. Of particular interest are those non-aqueous hydroformylation reactions designed to produce aldehydes at low pressures, such as disclosed, e.g. in U.S. Pat. Nos. 3,527,809; 4,148,830; 4,247,486; and 4,731,486.

Commercial experience has shown that, even in the substantial absence of extrinsic catalyst poisons, rhodium - tertiary organophosphine complex catalysts lose activity (i.e. become partially deactivated) during the course of continued prolonged hydroformylation and such is commonly referred to as intrinsic deactivation. While it is difficult to ascertain the precise reasons for such loss in activity, such deactivation is believed to be due in a large part to the combined effects of a number of processing conditions, e.g. reaction temperature, reactant partial pressures, the phosphine ligand, the ligand to rhodium mole ratio, and rhodium concentration employed. Since the variables significant for such catalyst instability are also variables essential for the hydroformylation, obviously such deactivation can not be totally avoided although it can be controlled or minimized. However, eventually the activity of the catalyst will decrease to such a point that it is no longer desirable to operate the hydroformylation process and the catalyst will either have to be reactivated or discharged and replaced with fresh catalyst.

Another potential problem for continuous hydroformylation processes is the accumulation of aldehyde condensation by-products of low volatility relative to the organophosphine ligand. Since commercial processes rely on vaporization or distillation to separate the reaction product medium containing the rhodium - ligand complex from the desired aldehyde hydroformylation products, the accumulation of high boiling aldehyde condensation by-products having a low volatility must be accounted for when designing the hydroformylation process.

When continuously hydroformylating lower olefinic compounds, the accumulation rate of high boiling aldehyde condensation by-products normally is low enough to be easily controlled. Thus, in the case of hydroformylating lower olefins, catalyst life mainly is limited by the rate of catalyst deactivation. However, in such systems when the level of deactivated rhodium species rises to undesirable values and it is no longer considered economical to continue the hydroformylation process, it may become expedient simply to replace the catalyst charge completely. Because rhodium is an expensive metal, however, it is uneconomical to discard the spent catalyst and a usual practice is for the catalyst to be reactivated.

Continuous hydroformylation of higher olefinic compounds, such as higher alpha-olefins, containing e.g., from six to thirty carbon atoms, using conventional organic (non-polar) solvent-solubilized non-ionic organophosphorus ligands, involves a further problem since aldehyde condensation by-products, having a low volatility relative to the organophosphorus ligands, accumulate at a much higher rate than encountered during the hydroformylation of lower olefins. Unfortunately the high rate of accumulation of such high boiling aldehyde condensation by-products cannot be readily controlled by removing same by distillation from the catalyst solution during the hydroformylation without incurring significant energy costs and exposing the catalyst to severe temperature conditions. Thus, it may be more practical to let such hydroformylations of higher olefins to merely run their course until the accumulation of such by-products becomes so great as to overwhelm the catalyst solution and economically prevent its further usefulness, at which time the catalyst solution needs to be replaced with a fresh catalyst solution.

There remains, however, the problem of recovering the rhodium values from said overwhelmed catalyst solution that is replaced. Again, unfortunately, due to their low volatility, the removal of such by-products from the replaced hydroformylation catalyst solution using conventional distillation techniques is plagued by the same energy-related and thermal exposure problems referenced above.

Assignee's U.S. Patent Application Ser. No. 231,508, entitled CATALYTIC METAL RECOVERY FROM NON-POLAR ORGANIC SOLUTIONS filed Aug. 12, 1988 in the names of David J. Miller and David R. Bryant (the entire disclosure of which is encompassed herein) is directed to solving the above problem by a novel method for recovering rhodium from organic solutions containing coordination complexes of rhodium and non-ionic organophosphine ligands. For example, the method encompasses contacting an organic solution containing a partially deactivated rhodium - tertiary non-ionic organophosphine complex hydroformylation catalyst with an aqueous solution containing an ionic organophosphine ligand to transfer the rhodium from said organic solution into said aqueous solution, and, if desired, subsequently transferring (e.g., back extracting) the rhodium from said aqueous solution into an organic solution containing a non-ionic organophosphine ligand for reuse in a hydroformylation process.

While not intending to be bound by any particular explanation or theory, it appears that the organic solvent - soluble and water-insoluble partially deactivated rhodium - tertiary non-ionic organophosphine hydroformylation complex catalyst is converted into a water-soluble rhodium - tertiary ionic organophosphine ligand complex product during contact between the organic and aqueous solutions, and thus the rhodium is extracted in the form of a water-soluble coordination complex.

In any event the amount of rhodium capable of being so extracted from its organic solution into the aqueous solution may depend on the degree of deactivation of the partially deactivated rhodium - tertiary non-ionic organophosphine complex hydroformylation catalyst present in the organic solution starting material. For example it appears that the more highly deactivated the rhodium complex catalyst, the lower the amount of rhodium capable of being so extracted. Thus obviously any method which would improve the amount of rhodium capable of being so extracted would be highly beneficial to the art.

DISCLOSURE OF THE INVENTION

It has now been discovered that the amount of rhodium, that is capable of being so extracted, can be increased or improved by pretreating the organic solution with certain organic reagents to obtain an organic reagent treated solubilized rhodium - tertiary non-ionic organophosphine complex product.

Such a method potentially has application in the wide variety of homogeneous catalysis applications noted earlier, and particularly for removing rhodium from organic solutions in which large concentrations of hard-to-remove components have accumulated, such as the high boiling aldehyde condensation by-products that accumulate during the hydroformylation of higher olefinic compounds.

Thus it is an object of this invention to provide a process for obtaining an organic solution of an organic reagent treated solubilized rhodium - tertiary non-ionic organophosphine complex product that contains more rhodium capable of being extracted into an aqueous solution containing an ionic organophosphine ligand, than contained in the partially deactivated rhodium - tertiary non-ionic organophosphine complex catalyst containing organic solution starting material of this process invention. Other objects and advantages of this invention will become readily apparent from the following description and appended claims.

The present invention is considered to have broad applicability to the recovery of rhodium from organic solutions containing partially deactivated rhodium - tertiary non-ionic organophosphine complex catalysts as for example may be formed inter alia in hydrogenating unsaturated compounds, such as in the hydrogenation of copolymers of a conjugated diene and co-polymerizable monomers as described in U.S. Pat. Nos. 4,464,515 and 4,503,196, in carbonylating methanol to acetic acid, in oligomerizing olefins, in hydrocyanating butadiene to adiponitrile, in decarbonylating aldehydes and in hydrosilylating olefins. For convenience in presentation, however, this invention will be described hereinafter with specific reference to the preferred recovery of rhodium from organic solutions of partially deactivated rhodium - tertiary non-ionic organophosphine complex catalysts used, for example, in hydroformylating olefinic compounds. The broad applicability of the present invention will nonetheless be appreciated and understood by those skilled in the art in view of the following description and specific examples.

Accordingly a generic aspect of this invention can be described as a process for increasing the amount of rhodium capable of being extracted into an aqueous solution containing an ionic organophosphine ligand, which rhodium is present in an organic solution containing a partially deactivated rhodium - tertiary non-ionic organophosphine complex complex catalyst, said process comprising mixing under non hydroformylation conditions, said organic solution with an organic reagent selected from the group consisting of (a) alkyne compounds having the formula $R-C\equiv C-CH_2-X$, (b) alkene compounds having the formula $(R^1)(R^2)C=C(R^3)-CH_2-X$, (c) diketene, (d) methyl halides, (e) methyl sulfonates, (f) propiolate compounds having the formula $HC\equiv C-C(O)OR^{14}$, and (g) oxide compounds having the formula

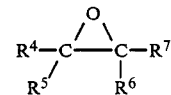

wherein X represents a radical selected from the group consisting of halogen atoms, a hydroxy radical, a carboxylate radical of the formula $-OC(O)R^8$, a sulfonate radical of the formula $-OSO_2R^8$ and a phosphonium radical of the formula $[-P^+(R^8)_3][Y-]$; wherein $R^8$ in the above formulae for X, each individually represent a monovalent hydrocarbon radical having from 1 to 18 carbon atoms selected from the group consisting of alkyl, aryl, aralkyl, alkaryl and cycloalkyl radicals and wherein Y represents an anion; and wherein each R, $R^1$, $R^2$, $R^3$, $R^4$, $R^5$, $R^6$, $R^7$, and $R^{14}$ radical individually represents a radical selected from the group consisting of hydrogen and a monovalent hydrocarbon radical having from 1 to 18 carbon atoms (e.g. alkyl, aryl, alkaryl, aralkyl and cycloalkyl radicals), with the following provisos: that $R^8$ in the above carboxylate formula can also be hydrogen; that $R^2$ and $R^3$ in the above formula for the alkene compounds can also be bonded together to form a five or six membered heterocyclic ring or monocyclic hydrocarbon ring along with the C=C group shown in said formula; and wherein any two of said $R^4$, $R^5$, $R^6$ and $R^7$ groups in the above formula for the oxides can be bonded together to form a five or six membered monocyclic hydrocarbon ring along with the C-C group shown in said formula; to obtain an organic solution of an organic reagent treated solubilized rhodium - tertiary non-ionic organophosphine complex product that contains more rhodium correspondingly capable of being extracted into an aqueous solution containing an ionic organophosphine ligand than contained in the partially deactivated rhodium - tertiary non-ionic organophosphine complex catalyst containing organic solution starting material of this process, said partially deactivated complex catalyst preferably being a hydroformylation catalyst.

DESCRIPTION OF THE PREFERRED EMBODIMENTS

As noted above the subject invention resides in the discovery that the amount of rhodium present in an organic solution of a partially deactivated rhodium - tertiary non-ionic organophosphine complex hydroformylation catalyst which is capable of being extracted into an aqueous solution containing an ionic organophosphine can be improved or increased by the process of this invention.

The solubilized partially deactivated rhodium - tertiary non-ionic organophosphine complex catalyst contained in the organic solution treated in accordance with this invention can be any such catalyst complex resulting from the wide variety of homogeneous catalysis processes noted earlier, and particularly from a hydroformylation process directed to producing aldehydes by hydroformylating an olefinic compound with carbon monoxide and hydrogen in the presence of a rhodium - tertiary non-ionic organophosphine complex catalyst, and which process has been operated to the extent that the originally employed catalyst complex has become at least partially deactivated, i.e. a catalyst which has become less reactive than its original counterpart. The extent of such catalytic deactivation may be determined at any given time e.g., by comparing the hydroformylation conversion rate to aldehyde product based on such catalyst to the conversion rate obtained using fresh catalyst.

Moreover, the organic solution starting materials that can be treated in accordance with this invention may consist of only the partially deactivated rhodium - tertiary non-ionic organophosphine complex catalyst and an organic solvent for said complex catalyst. More preferably such organic solutions may comprise all or any part of the hydroformylation reaction medium and/or all or any part of the liquid catalyst recycle medium of the corresponding hydroformylation process that produced the partially deactivated rhodium - tertiary non-ionic organophosphine complex catalyst.

As pointed out by the above prior art, methods for hydroformylating olefinic compounds to produce aldehydes with a rhodium - tertiary non-ionic organophosphine complex catalyst are well known in the art. Thus it should be clear that the particular hydroformylation process for producing aldehydes from an olefinic compound, as well as the reaction conditions and ingredients of said hydroformylation process, which serve as a means for furnishing the solubilized partially deactivated rhodium - tertiary non-ionic organophosphine complex catalyst containing organic solution starting material of the present invention, are not critical features of the present invention.

In general preferred hydroformylation processes comprise reacting an olefinic compound with carbon monoxide and hydrogen in a reaction vessel and in the presence of a non-aqueous hydroformylation reaction medium comprising aldehyde products, a solubilized rhodium - tertiary non-ionic organophosphine complex catalyst, free tertiary non-ionic organophosphine ligand and an organic solvent for said catalyst and free ligand. In continuous hydroformylation reactions aldehyde products are constantly being removed, the rhodium - tertiary non-ionic organophosphine complex catalyst either remaining in the hydroformylation reaction medium in the reactor as in the case of a gas recycle operation (e.g. U.S. Pat. No. 4,247,486), or being recycled back to the reactor after removal of some of the liquid reaction medium from the reactor and separation of aldehyde product therefrom, as in the case of a liquid catalyst recycle operation (e.g. U.S. Pat. No. 4,148,830 and U.S. Pat. No. 4,731,486).

Thus the "organic solution" starting material as employed herein means any organic liquid medium comprising a partially deactivated rhodium - tertiary non-ionic organophosphine complex catalyst, and an organic solvent for said complex catalyst, and such liquid mediums may be derived from any of the wide variety of homogeneous catalysis processes noted earlier and particularly from a non-aqueous hydroformylation process.

Accordingly the organic solution starting materials employable herein preferably contain at least some amount of two and preferably at least three different main ingredients or components, i.e., the partially deactivated rhodium - tertiary non-ionic organophosphine complex catalyst and an organic solvent, and preferably free tertiary non-ionic organophosphine ligand, said ingredients preferably corresponding to those employed and/or produced by the hydroformylation process from whence the organic solution starting material may be derived.

Preferably said organic solution starting materials also contain at least some amount of the aldehyde product corresponding to the desired aldehyde product of the hydroformylation process from whence such organic solution may be derived, although it may be possible, to remove all of such aldehyde product prior to treating the organic solution by the process of this invention. Of course it is to be further understood that the organic solution startinq materials of this invention can contain minor amounts of additional ingredients such as those which have either been deliberately employed in the hydroformylation process or formed in situ during said process. Examples of such additional ingredients that can also be present include unreacted olefin starting material, and in situ formed type products, such as unreacted isomerized olefin, hydrogenated olefin (e.g. corresponding saturated hydrocarbons or paraffin by-products); in situ type by-products derived from the aldehyde products, such as high boiling aldehyde condensation by-products (as described e.g. in U.S. Pat. No. 4,148,830 and U.S. Pat. No. 4,247,486) and in situ type alkyl substituted phosphine ligand by-product (such as described e.g. in U.S. Pat. No. 4,260,828). Moreover, the organic solution starting materials of this invention are essentially non-aqueous, as a result of having been derived from an essentially non-aqueous, homogeneous hydroformylation process.

Accordingly it should be sufficient for the purpose of this invention to understand that whatever compounds are present during the process from which the organic solution starting materials of this invention can be derived, may also be correspondingly present in said organic solution starting materials of this invention.

Thus the particular partially deactivated rhodium tertiary non-ionic organophosphine complex catalyst present in the organic solution starting material to be treated in accordance with this invention can be any such corresponding conventional rhodium hydroformylation catalyst which has been employed in a hydroformylation reaction to the extent that it has become partially deactivated. Accordingly the particular partially deactivated rhodium - tertiary non-ionic organophosphine complex catalyst, as well as its amount in a given organic solution starting material of this invention may obviously correspond to and merely be dependent upon the particular rhodium - tertiary non-ionic organophosphine complex catalyst employed in and/or formed under the reaction conditions of the particular hydroformylation reaction from whence the organic solution starting material to be treated according to this invention has been derived. For example illustrative rhodium - tertiary non-ionic organophosphine complex catalysts and hydroformylation reactions, include e.g. those disclosed in U.S. Pat. Nos. 3,527,809; 4,148,830; 4,247,486; 4,283,562; 4,400,548; 4,482,749; 4,491,675; 4,593,127; PCT Application, Publication No. WO 80/01690 (published August, 1980); and the like, the entire disclosures of which are incorporated herein by reference thereto. Of course mixtures of different catalysts and non-ionic organophosphine ligands can be employed if desired. Moreover, as noted in said references, the hydroformylation processes are generally and preferably carried out in the presence of free tertiary non-ionic organophosphine ligand i.e. ligand that is not complexed with the rhodium complex catalyst employed. While it is generally preferred that the free ligand be the same as the tertiary non-ionic organophosphine ligand of the rhodium - tertiary non-ionic organophosphine complex catalyst, such is not necessary. Accordingly it is to be understood that in the case of the rhodium - tertiary non-ionic organophosphine complex catalyst, as well as in the case of the free tertiary non-ionic organophosphine ligand any conventional tertiary non-ionic organophosphine ligand, heretofore advanced for such hydroformylation purposes, such as disclosed e.g. by the above mentioned references, can be employed herein.

Accordingly illustrative tertiary non-ionic orqanophosphines that may be employed, either as the free ligand and/or as the ligand of the rhodium complex catalyst, include e.g. trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl bisphosphines and bisphosphine mono-oxides, and the like. Of course any of the hydrocarbon radicals of such tertiary non-ionic organophosphines may be substituted if desired, with any suitable substituent that does not unduly adversely affect the desired result of the hydroformylation process or this invention. Illustrative substituents that may be on the hydrocarbon radicals in addition of course to corresponding hydrocarbon radicals such as alkyl, aryl, aralkyl, alkaryl and cyclohexyl substitutents, may include for example silyl radicals such as —$Si(R^9)_3$; amino radicals such as —$N(R^9)_2$; acyl radicals such as —$C(O)R^9$, acyloxy radicals such as —$OC(O)R^9$; amido radicals such as —$CON(R^9)_2$ and —$N(R^9)COR^9$; sulfonyl radicals such as —$SO_2R^9$, alkoxy radicals such as —$OR^9$; thionyl radicals such as —$SR^9$, phosphonyl radicals such as —$P(O)(R^9)_2$, as well as, halogen, nitro, cyano, trifluoromethyl, hydroxy radicals, and the like, wherein each $R^9$ individually represents the same or different monovalent hydrocarbon radical having from 1 to 18 carbon atoms (e.g., alkyl, aryl, aralkyl, alkaryl and cyclohexyl radicals), with the proviso that amino substituents such as —$N(R^9)_2$, each $R^9$ taken together can also represent a divalent bridging group that forms a heterocyclic radical with the nitrogen atom, and in amido substituents such as —$C(O)N(R^9)_2$ and —$N(R^9)COR^9$ each $R^9$ bonded to N can also be hydrogen. Of course it is to be understood that any of the substituted or unsubstituted hydrocarbon radicals groups that make up a particular given tertiary non-ionic organophosphine may be the same or different.

Such tertiary non-ionic organophosphines and corresponding rhodium - tertiary non-ionic organophosphine complex catalysts and/or methods for their preparation are well known as seen e.g. by the above mentioned references. Preferred tertiary non-ionic organophosphines these having the formula $(R^{10})_3P$ wherein each $R^{10}$ individually represents a monovalent hydrocarbon radical containing from 1 to 18 carbon atoms selected from the alkyl, aralkyl, alkaryl, cycloalkyl and aryl radicals, as disclosed e.g., in U.S. Pat. Nos. 3,527,809 and 4,283,562, and the like.

Among the more preferred tertiary non-ionic organophosphines are triphenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, and the like. The most preferred ligand is triphenylphosphine (TPP), while the most preferred catalyst is a rhodium-TPP complex.

As seen by the above mentioned hydroformylation references, the rhodium complex catalysts are generally considered as consisting essentially of rhodium complexed with carbon monoxide and tertiary non-ionic organophosphine (generally corresponding to the free tertiary non-ionic organophosphine ligand also normally present in the reaction medium). The catalyst terminology "consisting essentially of" is not meant to exclude, but rather include the possibility of any other ligand which does not unduly adversely affect the hydroformylation process, complexed with the rhodium such as hydrogen which is also a ligand in addition to the carbon monoxide and tertiary non-ionic organophosphine, the hydrogen being derived from the hydrogen gas of the hydroformylation reaction, if not already present in the catalyst precursor. Such hydroformylation catalysts may be formed in situ during the hydroformylation reaction or preformed by methods known in the art. For example preformed rhodium hydridocarbonyl-tris (tertiary non-ionic organophosphines) may be introduced into the reaction medium of the hydroformylation reaction. Alternatively rhodium catalyst precursors such as rhodium carbonyl tertiary non-ionic organophosphine acetylacetonates, $Rh_2O_3$, $Rh_4(CO)_{12}$, $Rh_6(CO)_{16}$, $Rh(NO_3)_3$ or rhodium dicarbonyl acetylacetonate, and the like, may be introduced into the reaction medium of the hydroformylation reaction. In any event an active rhodium complex hydroformylation catalyst is present in the hydroformylation reaction medium under the conditions of hydroformylation.

However, it is to be noted that the successful practice of this invention does not depend and is not predicated on any explanation as to the exact structure or nature of the active rhodium complex catalyst species or as to the exact structure or nature of the partially deactivated rhodium catalyst species formed during the hydroformylation. Indeed such exact structures are not known with certainty. Clearly for the purpose of understanding this invention, it is sufficient to simply point out that the partially deactivated rhodium - tertiary non-ionic organophosphine complex catalysts present in the organic solution starting materials of this invention can be any such partially deactivated catalyst mixture resulting from the use of a corresponding active rhodium - tertiary non-ionic organophosphine complex catalyst in the hydroformylation reaction medium of the hydroformylation process from whence the particular organic solution starting material employable in the process of this invention is derived.

The amount of the partially deactivated rhodium - tertiary non-ionic organophosphine complex catalyst present in the organic solution starting materials of this invention may range from about one part per million (ppm), up to about 50,000 parts per million (ppm) or more, calculated as rhodium metal. In general the amount of such partially deactivated rhodium complex catalyst present in the organic solution starting material of this invention preferably corresponds to the amount of the rhodium - tertiary non-ionic organophosphine complex catalyst employed in the hydroformylation reaction medium of the hydroformylation process from whence the organic solution starting material may be derived and such amounts are commonly expressed in terms of the amount of rhodium present calculated as rhodium metal. In the more preferred low pressure non-aqueous hydroformylation processes, rhodium hydroformylation concentrations preferably do not exceed 500 ppm, calculated as rhodium metal, with concentrations of from about 50 up to 300 ppm, calculated as rhodium metal being even more preferred. Of course the organic solution starting materials of this invention may contain higher concentrations of rhodium than present in the hydroformylation reaction medium, and such may be readily obtained e.g. simply by concentrating the rhodium catalyst containing hydroformylation medium prior to employing same as the organic solution starting material of this invention Such concentration procedures e.g., may range from merely removing some of the aldehyde product on up to preparing very viscous rhodium containing concentrates such as taught e.g. in U.S. Pat. No. 4,297,239. Rhodium concentrations in the range of from about 5 to about 10,000 ppm, and more preferably from about 10 to about 1000 ppm, of rhodium, calculated as rhodium metal, should be sufficient for most hydroformylation processes and such corresponding amounts are preferably present in the organic solution starting materials of this invention.

As noted above the tertiary non-ionic organophosphine ligands defined herein are employed in this invention as both the ligand of the rhodium - tertiary non-ionic organophosphine complex catalyst as well as, the free tertiary non-ionic phosphine ligand that is also present in the organic solution starting materials of this invention. In a given situation such rhodium-phosphine complexes and free phosphine ligands of course will correspond to those employed in the hydroformylation process from which said organic solutions may be derived. In addition, it is to be understood that while the tertiary non-ionic organophosphine of the rhodium complex catalyst and free tertiary non-ionic organophosphine ligand present in the reaction medium of a given hydroformylation process are normally the same, different tertiary non-ionic organophosphine ligands, as well as, mixtures of two or more different tertiary non-ionic organophosphine ligands may be employed for each individual purpose, if desired. As in the case with the amounts of rhodium complex catalyst employed, the amount of free tertiary non-ionic organophosphorus ligand present in a given organic solution starting material of this invention will in general correspond to that amount of corresponding free ligand present in the hydroformylation process from which said liquid medium may be derived. For instance, since the hydroformylation process may be carried out in any excess amount of free tertiary non-ionic organophosphine ligand desired e.g., at least one mole of free tertiary non-ionic organophosphine ligand per mole of rhodium present in the reaction medium, the amount of free tertiary non-ionic organophosphine ligand present in a given organic solution starting material of this invention can also be any corresponding excess amount e.g., at least one mole of free tertiary non-ionic organophosphine ligand per mole of rhodium metal present in the liquid medium starting material.

In general an amount of free tertiary non-ionic organophosphine ligand of from about 2 to about 300, and preferably from about 5 to about 200 moles per mole of rhodium metal present in the reaction medium should be suitable for most hydroformylation processes. Accordingly, corresponding amounts of free tertiary non-ionic organophosphine ligand may be present in the organic solution starting materials of this invention.

The organic solution starting materials of this invention also contain an organic solvent generally corresponding to that employed for solubilizing the rhodium - tertiary non-ionic organophosphine complex catalyst and free tertiary non-ionic organophosphine ligand present in the reaction medium of the hydroformylation process from which said organic solution starting materials of this invention may be derived. Any suitable organic solvent which does not adversely interfere with the intended hydroformylation process or this invention can be employed. Such organic solvents are well known in the art and encompass both polar and non-polar organic solvents, such as compounds belonging to the general classes of alkanes, ethers, aldehydes, ketones, esters, amides and aromatics. Illustrative suitable organic solvents include those described e.g. in U.S. Pat. No. 3,527,809; 4,148,830; and 4,731,486. Of course, mixtures of one or more different solvents may be employed if desired. Moreover, the preferred solvents are aldehyde compounds corresponding to the aldehyde products of the hydroformylation process and/or higher boiling aldehyde condensation by-products such as described e.g. in U.S. Pat. No. 4,148,830 and 4,247,486. The amount of organic solvent present in the organic solution starting materials need only be that amount sufficient to solubilize the partially deactivated rhodium - tertiary non-ionic organophosphine complex catalyst and free ligand present in said starting material. In general such amounts of organic solvent may correspond to those amounts of solvent present in the reaction medium or catalyst containing recycle medium of the hydroformylation process from whence the organic solution starting materials of this invention may be derived.

Thus in general the amount of organic solvent present in the organic solution starting materials of this invention may range from about 5 to about 95 parts by weight based on the total weight of said organic solution starting material.

Finally as noted above, the organic solution starting materials of the process of this invention also preferably contain at least some amount of aldehyde product corresponding to the aldehyde product obtained by the hydroformylation process from whence said organic solution starting materials may be derived. Such aldehydes may contain from 3 to 31 carbon atoms and encompass the corresponding hydroformylation aldehyde products obtained upon hydroformylating olefinic compounds containing from 2 to 30 carbon atoms. Such olefinic compounds can be terminally or internally unsaturated and be of straight-chain, branched chain or cyclic structures, as well as be olefin mixtures, such as obtained from the oliqomerization of propene, butene, isobutene, etc., (such as so called dimeric, trimeric or tetrameric propylene, and the like, as disclosed e.g. in U.S. Pat. Nos. 4,518,809 and 4,528,403). Moreover such olefinic compounds may further contain one or more ethylenic unsaturated groups and of course mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described e.g., in U.S. Pat. Nos. 3,527,809; 4,731,486 and the like.

Illustrative olefinic unsaturated compounds are alpha-olefins, internal olefins, alkyl alkenoates, alkenyl alkanoates, alkenyl alkyl ethers, alkenols, and the like e.g., ethylene, propylene, 1-butene, 1-hexene, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-pentene, 2-hexene, 2-heptene, propylene dimers, propylene trimers, propylene tetramers, 2-ethyl hexene, 2-octene, styrene, 3-phenyl-1-propene, 1,4-hexadiene, 1,7-octadiene, 3-cyclohexyl-1-butene, allyl butyrate, methyl methacrylate, vinyl ethyl ether, vinyl methyl ether, allyl ethyl ether, n-propyl 7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenyl-benzene, eugenol, iso-eugenol, safrole, iso-safrole, anethol, 4-allylanisole, indene, limonene, beta-pinene, dicyclopentadiene, cyclooctadiene, camphene, linalool, and the like.

Accordingly illustrative aldehyde products include e.g., propionaldehyde, n-butyraldehyde, isobutyraldehyde, n-valeraldehyde, 2-methyl 1-butyraldehyde, hexanal, 2-methyl valeraldehyde, heptanal, 2-methyl 1-hexanal, octanal, 2-methyl-1-heptanal, nonanal, 2-methyl-1-octanal, 2-ethyl-1-heptanal, 3-propyl-1-hexanal, decanal, 2-methyl-1-nonanal, undecanal, 2-methyl-1-decanal, dodecanal, 2-methyl-1-undecanal, tridecanal, 2-methyl-1-tridecanal, 2-ethyl-1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonadecanal, 2-methyl-1-octadecanal, 2-ethyl-1-heptadecanal, 3-propyl-1-hexadecanal, eicosanal, 2-methyl-1-nonadecanal, heneicosanal, 2-methyl-1-eicosanal, tricosanal, 2-methyl-1-docosanal tetracosanal, 2-methyl-1-tricosanal, pentacosanal, 2-methyl-1-tetracosanal, 2-ethyl-1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Of course it is understood that the aldehyde product of an alpha olefin will normally be a mixture of the normal straight chain aldehyde and its branched chain aldehyde isomer obtained upon hydroformylating said olefin. Moreover, mixtures of totally different aldehyde products can be present in the organic solution starting materials employable in this invention, e.g., when such organic solutions are derived from a process that hydroformylates mixtures of totally different olefinic compounds, such as e.g., mixtures of alpha olefins and internal olefins or mixtures of two different alpha olefins. The preferred aldehyde products present in the hydroformylation reaction product compositions employable in this invention are those derived from hydroformylating alpha olefins, internal olefins and mixtures of such alpha and internal olefins.

The more preferred olefin starting materials are alpha olefins having from 2 to 20 carbon atoms and more preferably from 3 to 14 carbon atoms. As employed herein the term "alpha olefin" means unsubstituted olefins, thus excluding substituted olefins such as alkyl alkenoates, alkenyl alkanoates, alkenyl alkyl ethers, alkenols, and the like. Of course it is to be understood that commercial alpha olefins containing 4 or more carbon atoms may contain minor amounts of corresponding internal olefins and/or their corresponding saturated hydrocarbon and that such commercial olefins need not necessarily be purified from same prior to being hydroformylated.

The amount of aldehyde product present in the organic solutions employable as the starting materials of this invention may range from 0 to about 90 percent by weight or higher of the liquid medium. Such amounts are not narrowly critical and will of course in general merely be dependent upon the particular reaction conditions and efficiency of the hydroformylation process from whence the organic solution starting materials of this invention may be derived. In general, preferred hydroformylation processes are those capable of producing a hydroformylation reaction product medium containing from about 10 to about 80 percent by weight of aldehyde product. Preferably the amount of aldehyde product present in the liquid medium starting materials employable in this invention may range from 0 to about 80 percent by weight, and more preferably from about 1 to 60 percent by weight, of the organic solution.

More preferably the organic solution starting materials of this invention correspond to all or a part of the reaction medium of a hydroformylation process as outlined herein or correspond to all or a part of the liquid catalyst containing recycle medium of such a hydroformylation process (i.e. that liquid catalyst containing residue obtained, after the removal of that desired amount of aldehyde product from the hydroformylation reaction product medium outside of the hydroformylation reactor or hydroformylation zone), which is recycled to the reactor in order to establish a continuous hydroformylation catalyst recycle process.

Of course it is to be further understood that the organic solution starting materials of this invention may also contain additional ingredients corresponding to those which have either been deliberately employed in the hydroformylation process from which said organic solution starting materials may be derived or which have been formed in situ during the hydroformylation process. For instance, obviously since an olefin starting material is being hydroformylated, the organic solution starting materials of this invention may contain some unreacted olefin starting material. The amount of such unreacted olefin present in any said organic solution starting material will be in general governed by the efficiency of the hydroformylation process. In general amounts of unreacted olefin may range from about 0 to about 20 percent by weight of the organic solution.

Likewise, minor amounts of in situ type by-products that may be formed during the hydroformylation process may also be correspondingly present in the organic solution starting materials of this invention, e.g., in situ type by-products derived from the olefinic starting materials, such as unreacted isomerized olefin, hydrogenated olefin (e.g., corresponding saturated hydrocarbons or paraffin by-products); in situ type by-products derived from the aldehyde products, such as high boiling aldehyde condensation by-products (as described e.g. in U.S. Pat. No. 4,148,830 and said U.S. Pat. No. 4,247,486 discussed above); and possibly even some in situ type alkyl substituted phosphorus ligand by product. Further minor amounts of other additional co-solvent type diluents or additives, if employed in the hydroformylation process, may correspondingly be present in the organic solution starting materials of this invention. Accordingly, it should be sufficient for the purpose of this invention to understand that whatever compounds are present in the hydroformylation reaction medium of the hydroformylation process from which the organic solution starting material of this invention is derived, may also be correspondingly present in said organic solution starting materials.

Likewise, the reaction conditions for effecting such hydroformylation processes may be those heretofore conventionally used and may comprise a reaction temperature of from about 45° C. to about 200° C. and pressures ranging from about 1 to 10,000 psia.

The total gas pressure of hydrogen, carbon monoxide and olefinic unsaturated starting compound of such hydroformylation processes may range from about 1 to about 10,000 psia, while it is preferred that the process be operated at a total gas pressure of hydrogen, carbon monoxide and olefinic unsaturated starting compound of less then about 1500 psia and more preferably less than about 500 psia. The partial pressure of the reactants is not particularly critical and depends predominately on the amount and nature of the reactants employed and the desired result to be obtained. For instance, in nonaqueous hydroformylation processes the carbon monoxide partial pressure is preferably from about 1 to about 120 psia and more preferably from about 3 to about 90 psia, while the hydrogen partial pressure is preferably about 10 to about 200 psia and more preferably from about 20 to about 160 psia. In general the $H_2:CO$ molar ratio of gaseous hydrogen to carbon monoxide may range from about 1:10 to 100:1 or higher, the more preferred hydrogen to carbon monoxide molar ratio being from about 1:1 to about 10:1. Further, it is more preferred to employ a hydroformylation reaction temperature of from about 60° C. to about 140° C.

It is to be further understood that while the subject invention is preferably directed to treating a organic solution that has been directly obtained from a hydroformylation process, the organic solution starting materials of this invention also encompass any subsequent organic solution derived from such an initial liquid medium so obtained, provided said subsequently derived organic solution also contains at least some amount of each of the two and preferably three main ingredients defined above i.e., the partially deactivated rhodium - tertiary non-ionic organophosphine complex catalyst and an organic solvent for said complex catalyst and preferably the free tertiary non-ionic organophosphine ligand and more preferably also at least some amount of the aldehyde product.

As noted above the organic reagents employable in the process of this invention can be any such reagent selected from the group consisting of (a) alkyne compounds having the formula $R-C\equiv CH_2-X$, (b) alkenes having the formula $(R^1)(R^2)C=C(R^3) CH_2-X$, (c) diketene, (d) methyl halides, (e) methyl sulfonates, (f) propiolate compounds having the formula $HC\equiv C-C(O)OR^{14}$, and (g) oxide compounds having the formula

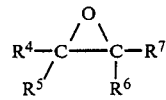

wherein R, $R^1$, $R^2$, $R^3$, $R^4$, $R^5$, $R^6$, $R^7$, $R^{14}$ and X are the same as defined above. More preferably each R, $R^1$, $R^2$, and $R^3$ radical represents hydrogen.

Illustrative monovalent hydrocarbon radicals having from 1 to 18 carbon atoms represented by the $R^1$, $R^2$, $R^3$, $R^4$, $R^5$, $R^6$, $R^7$, and $R^{14}$ and radicals in the above formulae include alkyl radicals such as methyl, ethyl, propyl, butyl, tertiary butyl, hexyl, etc.; aryl radicals such as phenyl, naphthyl, etc.; aralkyl radicals such as phenylethyl, benzyl, etc.; alkaryl radicals such as tolyl, xylyl, etc.; and cycloalkyl radicals, such as cyclohexyl, etc. Preferred monovalent hydrocarbon radicals are those containing from 1 to 8 carbon atoms, and more preferably they are phenyl or alkyl radicals, especially alkyl. Of course it is to be further understood that such hydrocarbon radicals represented by the radicals R through $R^7$ and $R^{14}$ may also be substituted with one or more substitutents that do not unduly adversely affect the desired purpose of this invention. Illustrative substitutents that may be present on such hydrocarbon radicals, in addition of course to additional corresponding hydrocarbon radicals such as alkyl, aryl, aralkyl, alkaryl and cycloalkyl substitutents, may include for example silyl radicals such as $-Si(R^9)_3$; amino radicals such as $-N(R^9)_2$; acyl radicals such as $-C(O)R^9$; acyloxy radicals such as $-OC(O)R^9$; amido radicals such as $-CON(R^9)_2$ and $-N(R^9)COR^9$; sulfonyl radicals such as $-SO_2R^9$; alkoxy radicals such as $-OR^9$; thionyl radicals such as $-SR^9$; phosphonyl radicals such as $-P(O)(R^9)_2$, as well as, halogen, nitro, cyano, trifluoromethyl, hydroxy radicals, and the like, wherein each $R^9$ individually represents the same or different monovalent hydrocarbon radical having the same meaning as defined for R to $R^7$ above, with the proviso that amino substituents such as $-N(R^9)_2$, each $R^9$ taken together can also represent a divalent bridging group that forms a heterocyclic radical with the nitrogen atom, and in amido substituents such as $-C(O)N(R^9)_2$ and $-N(R^9)COR^9$ each $R^9$ bonded to N can also be hydrogen. Of course it is to be understood that any substituted or unsubstituted hydrocarbon groups that make up a particular given organic reagent may be the same or different.

As noted above X may represent a hydroxy radical, i.e., $-OH$, or a halide atom. Illustrative halide atoms represented by X in the above formulae include chlorine, bromine and iodine, especially chlorine. Illustrative monovalent hydrocarbon radicals having from 1 to 18 carbon atoms represented by $R^8$ in the above formula for X include alkyl radicals, such as methyl, ethyl, propyl, butyl, tertiary butyl, hexyl, etc.; aryl radicals such as phenyl, naphthyl, etc.; aralkyl radicals such as benzyl, phenylethyl, etc.; alkaryl radicals, such as tolyl, xylyl, etc. and cycloalkyl radicals such as cyclohexyl, etc. Preferred monovalent hydrocarbon radicals are those containing from 1 to 8 carbon atoms such as benzyl or phenyl radicals, and more preferably alkyl radicals, especially methyl. Of course it is to be further understood that such hydrocarbon radicals of $R^8$ may also be substituted with one or more substitutents that do not unduly adversely affect the desired purpose of this invention. Illustrative substitutents that may be present on such $R^8$ hydrocarbon radicals, in addition of course to corresponding hydrocarbon radicals such as alkyl, aryl, aralkyl, alkaryl and cyclohexyl substituents, may include for example silyl radicals such as —Si$(R^9)_3$; amino radicals such as —N$(R^9)_2$; acyl radicals such as —C(O)$R^9$; acyloxy radicals such as —OC(O)$R^9$; amido radicals such as —CON$(R^9)_2$ and —N$(R^9)$CO$R^9$; sulfonyl radicals such as —SO$_2R^9$; alkoxy radicals such as —O$R^9$; thionyl radicals such as —S$R^9$; phosphonyl radicals such as —P(O)$(R^9)_2$, as well as, halogen, nitro, cyano, trifluoromethyl, hydroxy radicals, and the like, wherein each $R^9$ individually represents the same or different monovalent hydrocarbon radical having the same meaning as defined for $R^8$ above, with the proviso that amino substituents such as —N$(R^9)_2$, each $R^9$ taken together can also represent a divalent bridging group that forms a heterocyclic radical with the nitrogen atom, and in amido substitutents such as —C(O)N$(R^9)_2$ and —N$(R^9)$CO$R^9$ each $R^9$ bonded to N can also be hydrogen. Preferred substituents include e.g., cyano and —C(O)CH$_3$.

Illustrative anions represented by Y in the above phosphonium radical formula include halogen e.g., chlorine, bromine, etc.; sulfonic acids; acetic acids; and the like.

Preferred organic reagents are those of the above formulae for said propiolate compounds and said alkyne and alkene compounds wherein X represents a halide, hydroxy, carboxylate or sulfonate radical, more preferably the alkyne and alkene compounds.

Illustrative alkyne compounds that may be employed as the organic reagent of the process of this invention include e.g., propargyl formate, propargyl acetate, propargyl propionate, propargyl butyrate, propargyl cyanoacetate, propargyl acetoacetate, propargyl chloride, propargyl bromide, propargyl iodide, propargyl benzene sulfonate, propargyl triphenylphosphonium bromide, propargyl alcohol, and the like. The preferred alkyne compounds are alkyne alcohols and halides (e.g. wherein X in the above formula is a hydroxy radical or a halide radical) especially propargyl alcohol and propargyl halides, e.g. propargyl chloride, and those of the formula RC≡CCH$_2$OC(O)$R^8$ wherein R and $R^8$ are the same as defined above, especially propargyl acetate.

Illustrative alkene compounds that may be employed as the organic reagent of the process of this invention include e.g. allyl acetate, allyl propionate, allyl butyrate, allyl methacrylate, furfuryl acetate, allyl trifluroacetate, benzyl bromide, benzyl acetate, allyl chloride, allyl bromide, allyl iodide, allyl benzene sulfonate, allyl cyanoacetate, allyl triphenylphosphonium bromide, and the like. The preferred alkene compounds are those of the formula $R^1R^2$C=C$(R^3)$—CH$_2$—X wherein $R^1$, $R^2$, and $R^3$ are the same as defined above and X represents halogen or a carboxylate of the formula —0(CO)$R^8$ wherein $R^8$ is the same as defined above, and more preferably allyl halides and carboxylates, especially allyl acetate and allyl chloride.

Illustrative propiolate compounds that may be employed as the organic reagent of the process of this invention include e.g., methyl propiolate, ethyl propiolate, propyl propiolate, butyl propiolate, isobutyl propiolate, pentyl propiolate, hexyl propiolate, phenyl propiolate, and the like. The preferred propiolate compounds are those having the above formula wherein $R^{14}$ represents a monovalent hydrocarbon radical as defined above, especially alkyl. The more preferred propiolate compounds are methyl and ethyl propiolates.

Illustrative methyl halides and methyl sulfonate organic reagents that may be employable in the process of this invention include e.g., methyl chloride, methyl bromide, methyl benzene sulfonate, and the like.

Illustrative oxide compounds that may be employable in the process of this invention, include e.g., cyclohexene oxide, cyclopentene oxide, ethylene oxide, propylene oxide, styrene oxide, and the like.

The diketene organic reagent may be depicted by the formula:

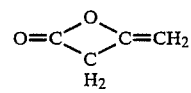

More particularly, the treatment of the organic solution starting material of this invention, which is conducted under non-hydroformylation conditions, i.e., in the essential absence of syn gas (CO+H$_2$), can be accomplished by mixing an organic reagent of choice with the desired organic solution starting material to obtain an organic solution of an organic reagent treated solubilized rhodium - tertiary non-ionic organophosphine complex product. The manner of said mixing of the organic reagent with the organic solution starting material and the order of addition is not critical and such can be carried out in any conventional fashion using any suitable equipment and technique, the preferred result merely being a through inclusion of the organic reagent in the organic solution. In general merely adding the organic reagent to the organic solution and gently stirring the solution should be sufficient to accomplish the desired result.

Moreover in view of the fact that the subject invention is directed to obtaining at least some desired improvement, with regard to increasing the amount of rhodium of the partially deactivated rhodium - tertiary non-ionic organophosphine complex catalyst contained in the organic solution to be treated, that is correspondingly capable of being extracted into an aqueous solution of an ionic organophosphine ligand and because the partially deactivated catalysts in said organic solution starting materials can vary both in terms of their nature and concentrations it is apparent no specific values can be arbitrarily given to such treatment conditions as e.g., the amount of reagent, pressure, temperature and contact time for said treatment that will encompass every given situation. Such conditions can vary greatly and are not narrowly critical and obviously need only be at least sufficient to obtain the result desired. For instance, in some cases a particular organic reagent may be more reactive than another and thus a smaller amount of the more reactive reagent may be beneficial, while in other circumstances a larger amount of the less reactive reagent may prove more desirable. Likewise treatment conditions such as temperature, pressure and contact time may also vary greatly and any suitable combination of such conditions may be employed herein. For instance, a decrease in any one of such conditions may be compensated for by an increase in one or both of the other conditions, while the opposite correlation is also true. In general the organic reagent may be added to and mixed with the organic solution starting material at liquid temperatures ranging from about 10°

C. to about 180° C., while temperatures ranging from about 20° C. to about 130° C. may be suitable in most instances. It is generally preferred to carry out said treatment at atmospheric (ambient) pressure, although higher or lower pressures may be employed if desired. Of course it is obvious that the contact time of the organic reagent and organic solution involved will be directly related to the particular partially deactivated rhodium - tertiary non-ionic organophosphine complex catalyst and particular organic reagent involved, as well as to such treatment conditions such as temperature, etc. and such contact time may vary from a matter of minutes to a few hours. Experience will determine the preferred temperature and contact time.

However, said treatment of the organic solution starting material with the organic reagent according to this invention must be under non-hydroformylation conditions, which is to say that of the process of this invention must be carried out in the essential absence of syn gas ($CO+H_2$), thus preventing any adverse simultaneous hydroformylation of the organic reagent and other compounds present in the organic solution starting material that is being employed. Preferably said addition and mixing is carried out under a nitrogen atmosphere, although mixtures of nitrogen and any other gas (except syngas) may be employed provided they do not unduly adversely affect the desired purpose of this invention. For example, hydrogen may be employed.

Of course the amount of organic reagent employed in of this invention need only be that minimum amount necessary to help achieve the desired end result of this invention. In general it is considered that the amount of organic reagent employed may range from about 0.1 up to about 1000 moles or higher per mole of rhodium, calculated as rhodium metal, in the organic solution starting material, although it is recommended to employ at least one mole of the organic reagent per mole of said rhodium. More preferably it is recommended that an excess molar amount of the organic reagent be employed although no added benefit is seen in employing very large excess amounts and very large excess amounts could be more detrimental than positive. In general it is considered that amounts of organic reagents ranging from about 0.5 to 500 moles per mole of rhodium, calculated as rhodium metal, in the organic solution starting material should be sufficient for most purposes, with preferred amounts being from about 1 to about 300 moles per mole of rhodium, calculated as rhodium metal.

In any event it is sufficient for the purpose of this invention to understand that the organic reagent is added and mixed with the organic solution starting material of this invention to obtain an organic solution of an organic reagent treated solubilized rhodium - tertiary non-ionic organophosphine complex product, which contains more rhodium correspondingly capable of being extracted into an aqueous solution containing an ionic organophosphine ligand than contained in the partially deactivated rhodium - tertiary non-ionic organophosphine complex catalyst in said organic solution starting material.

Thus it should be clear that while the selection of the optimum conditions of this invention to achieve the best results desired will be dependent upon one's experience in the utilization of the subject invention, in view of the disclosure and examples of this specification, only a certain measure of routine experimentation should be necessary in order to ascertain those conditions which are optimum for a given situation. However, it should also be clear that one of the beneficial factors involved in this invention as employed herein is the wide processing latitude that one has in selecting the proper combination of conditions that will be most useful in obtaining or at least best approaching a particular desired result or need.

Of course it is to be understood that the process of the subject invention is not directed to increasing the actual amount of rhodium over that contained in the organic solution starting material, but rather increasing the amount of rhodium correspondingly capable of being extracted into an aqueous solution containing an ionic organophosphine ligand. For instance, in any given organic solution of a partially deactivated rhodium - tertiary non-ionic organophosphine complex catalyst, X amount of rhodium can be extracted into a given aqueous solution containing an ionic organophosphine ligand y a given set of extraction conditions. This X amount of rhodium is referred to herein as the amount of rhodium capable of being extracted into an aqueous solution containing an ionic phosphine. However when said given organic solution of partially deactivated rhodium - tertiary non-ionic organophosphine complex catalyst is treated with an organic reagent according to this invention, X + Y amount of rhodium can be correspondingly extracted from the organic solution of the organic reagent treated solubilized partially deactivated rhodium - tertiary non-ionic organophosphine complex product into said given aqueous solution containing ionic organophosphine ligand by said given set of extraction conditions. This X + Y amount of rhodium then is evidence of the fact that the subject process of this invention has increased the amount of rhodium that is capable of being correspondingly extracted into an aqueous solution containing an ionic organophosphine ligand over that contained in the correspondingly untreated organic solution starting material.

While not intending to be held to any specific chemical theory or mechanistic discourse on just exactly how the beneficial desired result of the process of this invention is achieved, it is considered that intrinsic deactivation of the rhodium - tertiary non-ionic organophosphine catalyst is due at least in part to the in situ formation of rhodium complex clusters during the hydroformylation process, which clusters apparently decrease the amount of rhodium values capable of being extracted into an aqueous solution containing an ionic organophosphine ligand. It is further considered that in the process of this invention the organic reagent reacts with the rhodium of such clusters to form new rhodium complex species in the treated organic solution, which are apparently more susceptible to said extraction. In any event it has been found that the process of this invention results in obtaining an organic solution of an organic reagent treated rhodium - tertiary non-ionic organophosphine complex product that contains more rhodium correspondingly capable of being extracted into an aqueous solution containing an ionic organophosphine ligand than contained in the untreated partially deactivated rhodium - tertiary non-ionic organophosphine complex catalyst containing organic solution starting material of this invention.

Accordingly confirmation of such an improvement, obtainable by the process of this invention, can be witnessed by merely comparing the amount of rhodium extracted from a untreated organic solution containing a partially deactivated rhodium - tertiary non-ionic organophosphine complex catalyst into an aqueous solution containing an ionic organophosphine ligand via contacting the organic and aqueous solutions followed by phase separation of the organic and aqueous phases, against the amount of rhodium extracted from the corresponding organic solution of an organic reagent treated solubilized partially deactivated rhodium - tertiary non-ionic organophosphine product of this invention via the same extraction process, which procedure is illustrated in the following working examples given below.

Moreover, method of extracting rhodium from the organic solution of the organic reagent treated partially deactivated solubilized rhodium - tertiary non-ionic organophosphine complex product of this invention into an aqueous solution of an ionic organophosphine ligand is fully detailed in Assignee's U.S. Patent Application Ser. No. 231,508, entitled CATALYTIC METAL RECOVERY FROM NON-POLAR ORGANIC SOLUTIONS filed Aug. 12, 1988 in the names of David J. Miller and David R. Bryant (the entire disclosure of which is encompassed herein by reference thereto).

Thus said rhodium extraction process may comprise contacting all or part of said organic solution of an organic reagent treated solubilized rhodium - tertiary non-ionic organophosphine complex product of this invention with an aqueous solution of an ionic organophosphine ligand capable of forming a coordination complex with the rhodium to transfer rhodium from said organic solution into said aqueous solution.

For instance a suitable arrangement involves contacting the organic solution from which rhodium is to be extracted with an aqueous solution of the ionic phosphine ligand in any conventional extraction vessel.

In the extraction vessel, the organic solution is contacted intimately with the aqueous solution containing free water soluble ionic organophosphine ligand capable of forming a coordination complex with the rhodium. A wide variety of such ionic organophosphine ligands potentially can be used. Suitable water-soluble ionic organophosphine ligands that may be employed are those having the general formulae (1) and (2):

(1)

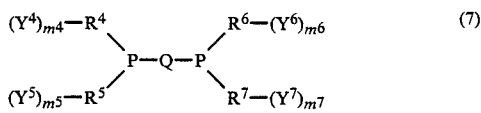
(7)

where $R^1$, $R^2$ and $R^3$ of formula (1) and $R^4$, $R^5$, $R^6$ and $R^7$ of formula (2) each individually represent a hydrocarbon radical containing from 1 to 30 carbon atoms selected from the group consisting of alkyl, aryl, alkaryl, aralkyl, and cycloalkyl radicals, where Q in formula (2) represents a divalent organic bridging group and where $Y^1$, $Y^2$ and $Y^3$ of formula (1) and $Y^4$, $Y^5$, $Y^6$, and $Y^7$ of formula (2) are are substituted on the hydrocarbon radical and each individually represents an ionic radical of overall neutral charge selected from the group consisting of:

—$SO_3M$ wherein M represents inorganic or organic cationic atoms or radicals selected so that the ligand is water-soluble, —$PO_3M$ wherein M represents inorganic or organic cationic atoms or radicals selected so that the ligand is water-soluble, —$NR_3X'$ wherein each R represents a hydrocarbon radical containing from 1 to 30 carbon atoms selected from the class consisting of alkyl, aryl, alkaryl, aralkyl and cycloalkyl radicals, and X' represents inorganic or organic anionic atoms or radicals selected so that the ligand is water-soluble, —$CO_2M$ wherein M represents inorganic or organic cationic atoms or radicals selected so that the ligand is water-soluble, Wherein $m^1$, $m^2$ and $m^3$ of formula (1) and $m^4$, $m^5$, $m^6$, and $m^7$ of formula (2) are integers which can be the same or different and which can range from 0 to 5. At least one of $m^1$, $m^2$ and $m^3$ and at least one of $m^4$, $m^5$, $m^6$ and $m^7$ cannot be zero (0), i.e., must be equal to or greater than 1, and must have a value sufficient to impart solubility in the aqueous solution the ligand. The integers $m^1$ through $m^7$ indicate the number of ionic radicals of overall neutral charge substituted on each hydrocarbon radical.

The hydrocarbon radicals, $R^1$, $R^2$ and $R^3$ of formula (1) and $R^4$, $R^5$, $R^6$, and $R^7$ of formula (2) preferably contain from 1 to 18 carbon atoms. Hydrocarbon radicals containing from 1 to 12 carbon atoms are more preferred. Such hydrocarbon radicals include those e.g. selected from the group consisting of alkyl, aryl, alkaryl, aralkyl and cycloalkyl. Illustrative hydrocarbon radicals are e.g. methyl, ethyl, propyl, butyl, hexyl, cyclohexyl, phenyl and the like. Most preferably at least one of $R^1$, $R^2$ and $R^3$ in formula (1) and at least one of $R^4$, $R^5$, $R^6$ and $R^7$ in formula (2) is a phenyl radical. Such hydrocarbon radicals may contain one or more substitutents provided that they do not unduly adversely affect the use of the ligand and this invention. Suitable substitutents, in addition to the necessary ionic substitutent, e.g., the sulfonate, carboxylate and the like, include straight and branched chain alkyl groups, preferably of 1 to 4 carbon atoms, alkoxy groups, halogen atoms, hydroxy, cyano, nitro and amino groups and the like. More preferably at least two, and most preferably three of $R^1$, $R^2$ and $R^3$ in formula (1) are phenyl groups and at least three and most preferably four of $R^4$, $R^5$, $R^6$ and $R^7$ in formula (2) are phenyl radicals.

The organic divalent bridging group represented by Q in the above formulas is a divalent radical containing from 1 to 30 carbon atoms selected from the group consisting of hydrocarbon radicals, oxygen containing hydrocarbon radicals (i.e. hydrocarbon radicals interrupted with an oxygen atom), sulfur containing hydrocarbon radicals (i.e. hydrocarbon radicals interrupted with a sulfur atom) and nitrogen containing hydrocarbon atoms (i.e. hydrocarbon radicals interrupted with a nitrogen atom). Preferably such radicals contain from 1 to 16 and more preferably from 1 to 12 carbon atoms. Illustrative divalent hydrocarbon radicals include alkylene radicals (e.g. methylene (—$CH_2$), ethylene, propylene, isopropylene, butylene, 1,2-dimethylethylene, t-butylene, neopentylene, 2-methylpropylene, hexylene, 2-ethylhexylene, dodecylene, eicosylene, and the like); arylene radicals (e.g. phenylene, substituted phenylene, diphenylene, substituted diphenylene, and the like); as well as alkylene containing arylene radicals (e.g. methylenephenylene (—$CH_2C_6H_4$—), (ethylenephenylethylene ($-C_2H_4C_6H_4-C_2H_4-$), phenylenepropylphenylene ($-C_6H_4C(CH_3)_2C_6H_4-$), methylenediphenylmethylene ($-CH_2C_6H_4C_6H_4CH_2-$), and the like: alkylidene radicals (e.g. ethylidene ($-CH=CH-$), and the like); and the like. Illustrative oxygen containing hydrocarbon radicals include alkyleneoxyalkylene radicals (e.g. ethyleneoxymethylene ($-C_2H_4OCH_2-$) propyleneoxymethylene ($-C_3H_6OCH_2-$), ethyleneoxyethylene ($-C_2H_4OC_2H_4-$), 1,2-bis(ethyleneoxy)ethane ($-C_2H_4OC_2H_4OC_2H_4-$), propyleneoxypropylene ($-C_3H_6OC_3H_6-$) and the like); aryleneoxyalkylene radicals (e.g. phenyleneoxymethylene ($-C_6H_4OCH_2-$), and the like); and the like. Illustrative sulfur or thio containing hydrocarbon radicals include alkylenethioalkylene radicals (e.g. ethlenethioethylene ($-C_2H_4SC_2H_4-$), 1,2-bis(ethylenethio)ethane ($-C_2H_4SC_2H_4SC_2H_4-$), propylenethiomethylene ($-C_3H_6SCH_2-$), propylenethiopropylene ($-C_3H_6SC_3H_6-$), and the like); arylenethioalkylene radicals (e.g. phenylenethiomethylene ($-C_3H_6S-CH_2-$), and the like); and the like. Illustrative amino containing hydrocarbon radicals include alkyleneaminoalkylene radicals (e.g. methyleneaminomethylethylene ($-CH_2N(CH_3)C_2H_4-$), ethyleneneaminomethylethylene ($-C_2H_4N(CH_3)C_2H_4-$), bis(ethyleneaminomethyl)ethane ($-C_2H_4N(CH_3)C_2H_4N(CH_3)C_2H_4-$), propyleneaminomethylpropylene ($-C_3H_6N(CH_3)C_3H_6-$) and the like; and the like. Most preferably Q is a divalent hydrocarbon radical, especially a divalent alkylene radical containing from 2 to 8 carbon atoms.

Particularly, suitable ionic organophosphine ligands are the ionic triarylphosphines and, in particular, the salts of sulfonated and carboxylated triarylphosphines, as, for example, are described in U.S. Pat. Nos. 4,248,802; 4,399,312; 4,668,824; 4,716,250 and 4,731,486; and European Patent Application Pub. No. 216,315 (published April, 1987). Preferred among this group are the salts of monosulfonated and of trisulfonated triphenylphosphines, and the salts of monocarboxylated and of tricarboxylated triphenylphosphine. Another suitable class of ionic organophosphines are ionic bisdiarylphosphines such as bisdiphenylphosphinoethane monosulfonate salts. Mixtures of suitable ionic phosphine ligands also can be employed.

Such water-soluble, ionic organophosphine ligands capable of forming a coordination complex rhodium embraced by the above formulae, as well as methods for their preparation, are well-known in the art and need not be described in detail. See for example *J. Chem. Soc.*(1958), pp. 276–288 and U.S. Pat. Nos. 4,248,802; 4,399,312; 4,483,802; 4,633,021; 4,668,824; 4,716,250 and 4,731,486, all incorporated herein by reference. For example sulfonated liquids may be prepared by sulfonating the corresponding phosphine, e.g. triphenylphosphine, with fuming sulfuric acid (oleum) under controlled temperature conditions.

The ionic phosphine ligands are used in their water-soluble salt form. As suitable counter-ions, M, for the anionic moieties of the ionic phosphine salts there can be mentioned the cations of the alkali and alkaline earth metals, e.g., lithium, sodium, potassium, cesium, rubidium, calcium, barium, magnesium and strontium, the ammonium cation and quarternary ammonium cations. Suitable anionic atoms or radicals include, for, example, sulfate, carbonate, phosphate, chloride, acetate, oxalate and the like. Of course it is understood that the number of anionic and cationic moieties in a ligand molecule also depends on the valences of the ions (ionic radical) and counter ions (M and X') of any particular ligand.

The water phase should contain an amount of the ionic organophosphine ligand sufficient to extract rhodium from the organic solution containing the solubilized organic reagent treated rhodium-teriary non-ionic organophosphorus complex product. If the solubility of the coordination complex formed as a result of the contacting is greater in the organic phase than in the water phase, then the particular ionic organophosphine used is not weil-suited for the extraction. Generally, routine experimentation can be used to determine the suitability of any particular ionic ligand as an extractant as well as to determine both a suitable concentration of the ionic ligand for the water extractant and suitable extraction conditions. Typically, the aqueous solution may contain a concentration of at least about 0.03 mol per liter of the soluble ionic organophosphine ligand and preferably at least about 0.1 mol per liter. Routine experimentation can be used to identify an optimum ratio. Normally, to ensure a satisfactory extraction of rhodium from the organic solution there should be sufficient ionic organophosphine ligand in the aqueous phase to yield a ratio of the molar concentration of organic solvent-soluble non-ionic ligand in the organic phase to the molar concentration of ionic ligand in the aqueous phase of below about 20, more generally below about 10 and most generally below about 5. For economic reasons, the highest molar concentration ratio of non-ionic ligand to ionic ligand that yields the desired extraction should be employed.

The upper limit of the water-soluble ionic ligand concentration is not critical and in part is determined by the solubility of the ionic ligand in water. However, since ultimate recovery of the rhodium likely will be accompanied by some loss of ionic ligand, too large an excess of ionic ligand preferably is to be avoided. Generally, based on economic considerations, a water-soluble ionic ligand concentration below about 0.3 mol per liter and, more usually below about 0.2 mol per liter, should be suitable in most circumstances.

The aqueous solution also may include other adjivants to facilitate the transfer (extraction) of rhodium into the aqueous phase. For example a neutral salt, e.g., sodium sulfate or phosphate, could be added to the aqueous phase to increase its density and thus facilitate its phase separation from the organic solvent phase.

While the organic solution and aqueous solution preferably are flowed countercurrent to one another in an extraction column, any other known extraction technique also could be employed. Thus, the aqueous extraction can be accomplished using a wide variety of known techniques and conventional equipment. Preferably, the aqueous extraction is carried out in a continuous manner using either continuous countercurrent multi-stage contacting procedures employing a series of mixer-settlers or a trayed column or by countercurrent differential contact in a packed tower, rotary-disc contacting column and the like. Equipment suitable for accomplishing the aqueous extraction will be apparent to those skilled in the art and need not be described in any detail.

A volume ratio of the organic solution (O) to the aqueous solution (A) introduced into the extractor, e.g. the extraction column, of from about 0.01 to 100 generally should be satisfactory for transferring rhodium into the aqueous phase, contacting (volume) ratios (0/A) between about 1 to 10 are more typical. An optimum value for any specific set of circumstances can be determined using routine experimentation.

The temperature for the contacting (aqueous extraction) also is not critical and to a certain extent depends upon the specific compositions of the organic solution and the aqueous solution. Generally, under atmospheric pressure operation, a temperature of from about ambient up to about 100° C. is satisfactory with a temperature from about ambient (e.g. 25° C.) to 60° C. being preferred. In any event, any condition of temperature and pressure at which the organic solution and the aqueous solution remain immiscible and in the liquid state can be employed.

The contacting time also is not critical and need only be sufficient to accomplish the desired extraction of the rhodium from the organic phase. A contact time between about 1 minute and 24 hours should prove adequate in most instances. A contact time between about 3 and 30 minutes is more typical. An appropriate contacting period can be determined using routine experimentation. This contacting of the aqueous solution and the organic solution causes rhodium to transfer from the organic solution into aqueous solution.

Organic solution recovered from the overhead of the extraction column may contain residual rhodium, organic solvent-soluble organophosphorus ligand and organic solvent, e.g., aldehyde product and higher boiling liquid aldehyde condensation by-products in the case of hydroformylation. If desired, this stream can be retreated separately to recover both residual organophosphorus ligand and residual rhodium. The aqueous solution recovered from the bottom of the extraction column will contain rhodium that was present in the original organic solution starting material.

By appropriately treating this aqueous solution, it is possible to transfer the rhodium back into an organic solvent, which in the specific case of hydroformylation should be suitable for reuse in a hydroformylation reaction medium as catalyst. For instance, the aqueous rhodium containing solution may be treated with a conditioning reagent, in order to reduce the amount, in the aqueous solution, of the water-soluble ionic organophosphine ligand capable of complexing with the rhodium. In other words, the aqueous solution is treated so that the complex-forming ability of the ionic ligand is rendered incapable or less capable of forming a coordination complex with rhodium. If desired, the concentration of rhodium in the aqueous solution can be concentrated, e.g. by vaporization, before or after treatment with the conditioning reagent. In any event, an aqueous solution generally will be obtained having a rhodium concentration of from about 1 to 50,000 ppm, and more typically between about 5 and 10,000 ppm, calculated as rhodium metal.

The aqueous rhodium containing solution can be treated with a variety of conditioning reagents in order to reduce the amount of (i.e. chemically degrade or alter) the ionic organophosphine ligand. For example, the aqueous solution can be treated with an yield precursor such as maleic acid, with a strong acid such as sulfuric acid, with an alkylating agent such as methyl iodide or with an oxidizing reagent such as hydrogen peroxide or an organic peroxide. The conditioning reagent should react with the water-soluble ionic ligand to produce products that lack a coordinating affinity for the rhodium. Preferably, the reaction products are water-soluble and organic solvent-insoluble so that they are not back-extracted into the organic solvent during subsequent treatment. Treatment with the conditioning reagent thus reduces the amount, in the aqueous solution, of ionic ligand capable of strongly coordinating with rhodium.

Although not particularly critical, the aqueous solution preferably is treated with the conditioning reagent at a temperature of between about 0° to 250° C. for a time between about 0.1 to 24 hours. In any event, the solution should be treated under conditions necessary to reduce the amount of ligand capable of complexing with the rhodium by an amount sufficient to permit back-extraction of rhodium into a organic solvent which contains an organic solvent-soluble and water-insoluble non-ionic organophosphorus ligand. A treatment temperature of about 25° to 60° C. for a time period of one to four hours should be adequate in most cases. It is preferred to reduce the amount of water-soluble ionic ligand by at least about 70% and preferably by at least about 85%. An amount of residual ionic ligand of below about 10 equivalents, i.e., 10 mols of ligand per gram atom of rhodium, and preferably below about 5 equivalents is especially preferred. Best results are obtained if the rhodium coordination ability of the water-soluble ionic ligand is completely destroyed.

Suitable yield precursors for use in the present invention as conditioning reagents are unsaturated compounds containing from 2 to 18 carbon atoms, preferably from 3 to 10 carbon atoms, and can be selected from the group consisting of unsaturated compounds having the formula

wherein Z is a radical selected from the group consisting of

—CN, —Cl, Br, —I, —NO$_2$, and OR$^{12}$; R$^{11}$ is a radical selected from the group consisting of hydrogen, alkyl, aryl, hydroxy, alkoxy, amino and halogen; R$^{12}$ is an alkyl or aryl radical; and R$^8$, R$^9$ and R$^{10}$ an individually are radicals selected from the group consisting of hydrogen, alkyl, aryl, Z radicals as defined above and —CH$_2$Z radicals wherein Z is the same as defined above; and wherein R$^8$ and R$^9$ taken together can form an alkylene group having from 2 to 8 carbon atoms; and anhydrides of the carboxylic acids of the unsaturated compounds within the scope of formula (A). Maleic acid and maleic anhydride are particularly useful reagents.

A strong acid conditioning reagent suitable for treating the aqueous solution may be an inorganic or organic acid. Such inorganic acids as hydrochloric, sulfuric, nitric, phosphoric and such organic acids such as methanesulfonic acid and para-toluenesulfonic acid are suitable. Many others will be apparent to those skilled in the art. Sulfuric acid is preferred. To an extent, treatment with a strong acid conditioning agent is reversible. Thus the complex-forming ability of water-soluble ionic ligand previously rendered incapable of forming a coordination complex with rhodium by treatment with the strong acid, can, by subsequent treatment with an appropriate alkaline reagent, such as sodium hydroxide, be restored.

Acceptable alkylating reagents for use as the conditioning reagent can be selected from the class of compounds capable of reacting with the water-soluble ionic organophosphine ligand to form a water-soluble phosphonium salt thereof. Compounds of this class are monovalent hydrocarbon halides, such as methyl iodide (see U.S. Pat. No. 4,429,161, the disclosure of which is incorporated herein by reference).

An oxidizing agent suitably employed in this invention as the conditioning reagent may be supplied in the form of a gas or liquid and can be selected from oxygen, hydrogen peroxide, and organic peroxides, metal oxidizing reagents and peracids which preferably form water-soluble oxidation by-products with the water-soluble organophosphine ligand. Hydrogen peroxide is a particularly suitable oxidizing agent. It is to be understood that oxygen need not be employed in its pure form, but more preferably and conveniently is employed in the form of air or in admixture with an inert gas, such as nitrogen in order to minimize any explosive hazards.

The liquid organic peroxides, which may also be employed as oxidants herein, preferably encompass water-soluble organic peroxides of the formula R—O—O—R′, wherein R represents a radical selected from the group consisting of monovalent hydrocarbon radicals of 2 to 20 carbon atoms, carboxylic acyl radicals of 2 to 20 carbon atoms, aroyl radicals of 7 to 20 carbon atoms and cycloalkoxycarbonyl radicals of 4 to 20 carbon atoms, and wherein R′ represents a radical represented by R as defined above. Preferred monovalent hydrocarbon radicals represented by R and R′ above are alkyl and aralkyl radicals, especially tertiary alkyl radicals of 4 to 20 carbon atoms and aralkyl radicals of 8 to 15 carbon atoms. Most preferably R′ represents hydrogen (i.e., —H). Illustrative organic peroxides include t-butyl hydroperoxide, t-amyl hydroperoxide, cumene hydroperoxide, ethylbenzene hydroperoxide, and the like. Such organic peroxides and/or methods for their preparations are well known in the art.

The aqueous solution recovered from this treatment having a lowered amount of rhodium complex-forming, water-soluble ionic organophosphine ligand then can be contacted (back-extracted) with an immiscible, non-polar, organic solvent containing a non-polar organic solvent-soluble and water-insoluble non-ionic organophosphorus ligand. The same non-polar organic solvent-soluble and water-insoluble non-ionic ligands previously described as being useful for hydroformylation can be employed. As with the first extraction, the contacting typically can be done in any suitable extraction vessel. Again, any substantially non-polar organic solvent which forms a separate, distinct phase in the presence of the aqueous phase, and, in the specific case of hydroformylation, which does not adversely (i.e., which is preferably compatible with) the desired hydroformylation reaction medium can be employed. Particular useful non-polar solvents are those known to be suitable for use in prior art hydroformylation processes as described previously herein. The non-polar organic solution used for back extraction preferably contains the same organic solvent-soluble, non-ionic organophosphorus ligand which is to be used in the hydroformylation reaction medium.

The non-polar organic solvent should contain an amount of the non-polar organic solvent-soluble, non-ionic organophosphorus ligand sufficient to back-extract rhodium from the treated aqueous solution. The necessary concentration of the non-polar organic solvent-soluble, non-ionic ligand will depend, interalia, on the nature and residual level of the water-soluble, ionic phosphine ligand in the aqueous phase, on the particular non-polar organic solvent-soluble non-ionic ligand and its amount in the organic solvent and on the extraction conditions. Generally, routine experimentation can be used to determine the suitability of any particular non-polar solvent-soluble, non-ionic ligand as a back extractant, as well as to determine both a suitable ligand concentration for the non-polar solvent and suitable extraction conditions. Typically, the non-polar organic solvent will contain about 0.01 to 1.0 mols per liter of the non-polar organic solvent-soluble, non-ionic organophosphorus ligand and normally will contain about 0.03 to 0.6 mols per liter. Normally to ensure a satisfactory extraction of rhodium from the aqueous solution, there should be sufficient non-polar organic solvent-soluble, non-ionic ligand in the organic solvent to yield a ratio of the molar concentration of non-polar organic solvent-soluble, non-ionic ligand in the organic solvent (non-ionic ligand) to the molar concentration of residual polar water-soluble ionic ligand capable of forming a coordination complex with rhodium in the aqueous phase (ionic ligand) of above about 10, preferably above about 20, and most preferably above about 30. Conditions and equipment for the back-extraction step can be the same as those employed in the initial organic-aqueous extraction used to transfer rhodium from the catalyst solution to the aqueous solution.

Thus the organic solution containing organic reagent treated solubilized rhodium - tertiary non-ionic organophosphine complex products of this invention can be readily employed as the starting materials for the aqueous extraction process outlined above and disclosed in Assignee's U. S. Patent Application Ser. No. 231,508. In turn the aqueous rhodium containing solutions derived therefrom can be used in the reaction mediums of aqueous hydroformylation processes or to serve as a means for preparing organic solvent containing back extracted rhodium - tertiary non-ionic phosphines complex compositions for use in the reaction mediums of non-aqueous hydroformylation processes.

Alternatively applicants have found that organic solutions containing certain organic reagent treated solubilized rhodium - tertiary non-ionic organophosphine complex products of this invention need not necessarily be extracted into an aqueous solution but can themselves become substantially active e.g., under hydroformylation conditions when subsequently used in non-aqueous hydroformylation catalysis as fully detailed for example in Assignee's U.S. Patent Application Ser. No. 231,510 entitled REACTIVATION OF HYDROFORMYLATION CATALYSTS filed Aug. 12, 1988 in the names of the same subject inventors of this application (the entire disclosure of which is encompassed herein by reference thereto).

Said copending application Ser. No. 231,510 discloses the invention of treating obtained organic solutions of the organic reagent treated solubilized rhodium - tertiary non-ionic organophosphine complex products of this invention, wherein the organic reagent employed is any of the above described organic reagents employable in this invention, except alkyne and alkene compounds of the wherein X is a hydroxyl (i.e. —OH) radical, to obtain a rhodium - tertiary non-ionic organophosphine complex hydroformylation catalyst having better catalytic hydroformylation activity than the partially deactivated rhodium - tertiary non-ionic organophosphine complex hydroformylation catalyst employed in the organic solution starting material of this invention.

The process comprises of eliminating from such organic solutions of the organic reagent treated solubilized rhodium - tertiary non-ionic organophosphine complex product any hydroformylation catalytic inhibitor formed by the process of this invention, to obtain a rhodium - tertiary non-ionic organophosphine complex hydroformylation catalyst that is more catalytically active than the partially deactivated rhodium - tertiary non-ionic organophosphine complex hydroformylation catalyst in the organic solution starting material of this invention, and such may be accomplished in a number of ways.

For instance, while not intending to be held to any specific chemical theory or mechanistic discourse on just exactly how such a beneficial desired result is achieved, it is considered that intrinsic deactivation of the rhodium - tertiary non-ionic organophosphine catalyst is due at least in part to the in situ formation of rhodium complex clusters during the hydroformylation process, which are catalytically inactive or less active than the active rhodium complex catalyst species, thus decreasing the amount of active rhodium values in the reaction medium. It is further considered that in the process of this invention the organic reagent reacts with the rhodium of such clusters to form new rhodium complex species in the treated organic solution. While the new rhodium complex species in the organic reagent treated solubilized rhodium - tertiary non-ionic organophosphine complex product has not been found to immediately exhibit improved catalytic activity over that of the partially deactivated rhodium - tertiary non-ionic organophosphine complex catalyst in the organic solution starting material, it is considered that such is due to a catalytic inhibitor formed during the organic reagent treatment. Said catalytic inhibitor is considered to be the acid moiety of the organic reagent which may be present in said treated complex product in its free form and/or as part of a new rhodium complex species formed by said treatment. In any event it has been found that the elimination of whatever form the catalytic inhibitor is present as, results in obtaining a rhodium - tertiary non-ionic organophosphine complex hydroformylation catalyst that is more catalytically active than the partially deactivated rhodium - tertiary non-ionic organophosphine complex hydroformylation catalyst in the organic solution starting material of the process of this invention. Again while not intending to be held to any specific chemical theory or mechanistic disclosure, it is considered that during and/or as a result of the elimination of such catalyst inhibitor, the organic reagent treated solubilized rhodium complex product, is somehow converted from an inhibited complex to a more active rhodium complex species.

Accordingly said process comprises eliminating from the organic solution of the organic reagent treated solubilized rhodium - tertiary non-ionic organophosphine complex product of this invention any hydroformylation catalytic inhibitor formed by the process of this invention to obtain a rhodium - tertiary non-ionic organophosphine complex hydroformylation catalyst that is more catalytically active, than the partially deactivated rhodium - tertiary non-ionic organophosphine complex hydroformylation catalyst in the organic solution starting material of this invention.

Said elimination of such a hydroformylation catalytic inhibitor may comprise either removing or neutralizing said hydroformylation catalytic inhibitor in any suitable manner as described more fully herein below.

For instance, it is to be understood that the particular procedure applicable may be governed and/or depend upon such factors as the particular organic solution starting material as well as the organic reagent employed.

One illustrative procedure may comprise removing such catalytic inhibitor by contacting the organic reagent treated organic solvent-solubilized rhodium - tertiary non-ionic organophosphine complex product of this invention with any suitable aqueous alkaline or buffer solution and phase separating the organic and aqueous phases of the result mixture to obtain an organic solubilized rhodium - tertiary non-ionic organophosphine complex hydroformylation catalyst product that is more catalytically active than the organic solubilized partially deactivated rhodium - tertiary non-ionic organophosphine complex hydroformylation catalyst contained in the organic solution starting material.

It is considered that any of the above mentioned organic reagents, except for alkyne alcohols and alkene alcohols, may be employable with this procedure, since it is considered that the catalytic inhibitor that is formed may be eliminated (removed) along with the aqueous phase during said phase separation. The improvement in hydroformylation catalytic activity of the obtained organic solubilized rhodium - tertiary non-ionic organophosphine complex product of said phase separation may then be confirmed by employing same in a non-aqueous hydroformylation process. Of course it is to be understood that such confirmation may or may not be immediately obtained upon the start up of such a non-aqueous hydroformylation process but may come about later after the non-aqueous hydroformylation has been continuously carried out for a while.

Yet another and even more preferred procedure merely comprises continuously hydroformylating the organic reagent treated solubilized rhodium - tertiary non-ionic organophosphine complex product of this invention to obtain a solubilized rhodium - tertiary non-ionic organophosphine complex hydroformylation catalyst product that is more catalytically active than the solubilized partially deactivated rhodium - tertiary non-ionic organophosphine complex hydroformylation catalyst contained in the organic solution starting material of this invention. This preferred procedure omits the need for the above discussed treatment with an aqueous alkaline or buffer solution of said product prior to such hydroformylation. However the success of this procedure may be dependent upon the type of organic reagent employed. For example it has been found that when the organic reagent is propargyl acetate, continuous non-aqueous hydroformylation of the treated product resulted in a hydroformylation process that exhibited improved catalytic activity above that obtained with the corresponding untreated partially deactivated rhodium - tertiary non-ionic organophosphine complex catalyst in the organic solution starting material. Accordingly it is considered that the use of mildly acidic organic reagents such as the alkyne and alkene compounds of the above formulae wherein X represents a carboxylate radical, as well as the organic reagent propiolate compounds and oxide compounds defined above, result in a relatively mild catalytic inhibitor which may be conveniently eliminated (removed) via continuous hydroformylation over time.

For example it is considered that when such mildly acidic organic reagents are employed the inhibitor formed may be gradually eliminated (removed) from the reaction medium of the continuous hydroformylation process e.g., via the recovery procedure used to obtain the desired aldehyde product thus resulting in the desired catalytically improved rhodium - tertiary non-ionic organophosphine complex catalyst. Said improvement in catalytic activity may be readily determined by analyzing for same during said continuous hydroformylation. As noted above such confirmation of improved activity may only be exhibited after the hydroformylation has been continuously carried out for a while.

Any suitable alkaline material may be employable for the aqueous alkaline solutions useful in the above discussed procedure. Illustrative alkaline materials that may be mentioned include e.g., the alkali metal and alkaline earth metal and ammonium salts of hydroxides, carbonates, and borohydride, such as sodium bicarbonate, sodium carbonate, sodium hydroxide, potassium hydroxide, lithium hydroxide, cesium hydroxide, barium hydroxide, calcium hydroxide, ammonium hydroxide, sodium borohydride, and the like, especially sodium bicarbonate.

Aqueous buffer containing solutions may also be useful the above discussed procedure. Illustrative buffer mixtures include salts of inorganic oxy acids, such as phosphine acid/monobasic phosphate/dibasic phosphate of an alkali metal, boric acid/borate of an alkali metal, and carbonate/bicarbonate of an alkali metal; e.g., equimolar mixtures of the monobasic phosphate and the dibasic phosphate of sodium or of potassium, or of the carbonate and the bicarbonate of sodium or of potassium. Of course it is to be understood that any suitable mixture of aqueous alkaline and buffer solution may be employed if desired The contacting of the organic solution of the organic reagent treated rhodium - tertiary non-ionic organophosphine complex product of this invention and such aqueous alkaline or buffer solutions may be carried out in any suitable manner using any suitable equipment. Such contact is carried out under non-hydroformylating conditions as explained above. For example the contact may be effected under non-hydroformylating conditions by simply mixing the aqueous alkaline or buffer solution with the treated organic solution product of this invention such as in a conventional washing procedure. It is preferred to contact, e.g, wash, the treated product of this invention with the aqueous alkaline or buffer solution when employed under non-hydroformylation conditions and preferably under nitrogen at atmospheric pressure. Non-hydroformylating contacting temperatures of from about 20° C. to about 100° C. and more preferably from about 25° C. to about 65° C. should be sufficient for most purposes, although lower or higher temperatures may be employed if desired. Normally the washing can be completed within a matter of minutes, and the organic and aqueous phases phases of the mixture separated in any desired conventional fashion.

The amount of alkaline or buffer material, when employed in the above discussed procedure, required to obtain the desired result is not particularly critical for it obviously need only be that amount sufficient to achieve at least some improvement, and naturally more preferably the best improvement, in catalytic activity of the particular partially deactivated rhodium - tertiary non-ionic organophosphine complex hydroformylation catalyst involved.

In general when employed under non-hydroformylating conditions aqueous alkaline or buffer solutions containing from about 0.1 to about 20% by weight of alkaline or buffer material and ranging from about 0.1 to about 1.5 parts by volume per part of treated product of this invention should be sufficient for most purposes. Illustrative preferred aqueous alkaline solutions may include from about 0.1 to about 0.5 parts by volume of a 5 to 10 weight percent aqueous sodium bicarbonate solution. Of course it is to be understood that when employed such aqueous alkaline or buffer solution washes could be carried out more than once if desired e.g., successive washings of the preceding obtained organic phases collected via phase separation from the aqueous phase, although it is believed that only one such washing should be sufficient for most purposes. Further as with any such conventional washing procedure, the obtained separated organic phase may be further washed with water one or more times if desired to remove any small amounts of alkaline or buffer material contained in said organic phase.

As described above such aqueous alkaline or buffer treatment procedures may be considered as being necessary for achieving any improvement in catalyst activity for the partially deactivated rhodium - tertiary non-ionic organophosphine complex hydroformylation catalyst involved, when the organic reagent used is either (i) an alkyne or alkene compound of the above formula wherein X represents either halogen, a sulfonate or phosphonium radical as defined above, (ii) a methyl halide compound or (iii) a methyl sulfonate compound.

Alternatively, when the organic reagent used is an alkyne or alkene compound of the above formula wherein X represents a carboxylate radical, or a propiolate compound or oxide compound as defined above, the preferred procedure may comprise merely continuously hydroformylating the treated organic product solution of this invention until at least a sufficient amount of the catalytic inhibitor has been eliminated in order to obtain a rhodium - tertiary non-ionic organophosphine complex hydroformylation catalyst that is more catalytically active than the partially deactivated rhodium - tertiary non-ionic organophosphine complex hydroformylation catalyst contained in the organic solution starting material.

Of course it is to be understood that such continuous hydroformylation processes, be they for reactivation and/or for confirmation of the desired improved catalytic activity are well known in the art, as seen already herein discussed above and contained in the above mentioned cited references. Accordingly any of such conventional continuous hydroformylation processes and conditions already disclosed and discussed herein may be employed for said reactivation and/or for confirmation of the desired improved catalytic activity and such processes and conditions obviously need not be further detailed again.

The exact time period of continuous hydroformylation required before any improvement in catalyst activity may be observed over that of the corresponding partially deactivated rhodium - tertiary non-ionic organophosphine complex catalyst employed will of course obviously vary depending upon the compounds and processing conditions involved. Thus obviously no arbitrary time period for such an accomplishment can, nor need be assigned for the elimination of the catalytic inhibitor by such continuous hydroformylation. Rather it is sufficient to understand that such may be accomplished merely by subjecting the treated organic product solution of this invention to continuous hydroformylation for a sufficient period of time until there is evidenced an improvement in the catalytic activity of the process over that obtainable using the corresponding partially deactivated rhodium - tertiary non-ionic organophosphine complex catalyst of the organic solution starting material of this invention. In general it is preferred that some improvement in catalyst activity should be evidenced within at least a few hours or earlier. Of course it is to be understood that any improvement in catalyst activity should continue to get better with time until the maximum improvement possible is obtained.

Again the continuous hydroformylation procedures employable are not critical and any known conventional procedure that achieves the desired result may be employed. Preferred continuous hydroformylation processes are those involving a liquid catalyst recycle process wherein one need only treat all or a part of the reaction medium or all or part of the liquid catalyst containing recycle medium according to the process of this invention and then continue to employ the same hydroformylation process.

Further, improved regenerated hydroformylation catalytic activity may be determined by any suitable method such as e.g., by measuring the rates of reaction of the partially deactivated rhodium complex catalyst in the organic solution starting material and the organic reagent treated rhodium complex product of this invention as compared the activity of a fresh rhodium complex catalyst employed in the same manner. This effect may be easily determined by carrying out the hydroformylation reactions and by continuously monitoring the rate of hydroformylation. The difference in hydroformylation rate (or difference in catalyst activity) may then be observed in a convenient laboratory time frame.

Thus a particularly preferred and beneficial aspect of this invention may comprise merely stopping a rhodium organophosphine catalyzed continuous hydroformylation reaction which has been conducted in a reaction vessel (reactor) for a period of time sufficient to partially deactivate the catalyst and treating, under non-hydroformylation conditions, the hydroformylation reactor medium with an appropriate organic reagent while said reaction medium remains in the reactor, and thereafter merely restarting the same continuous hydroformylation process to obtain a desired hydroformylation catalyst that is more catalytically active than the partially deactivated catalyst contained in said untreated reaction medium. The hydroformylation reaction can be stopped by any convenient method e.g., by merely stopping the feed of the reactant gases (olefin, carbon monoxide and hydrogen) to the reaction vessel and clearing the recycle lines of the reaction system. The appropriate organic reagent, e.g., propargyl acetate, may then be added to the reaction medium in the reactor in any appropriate manner and mixed therein followed by restarting the hydroformylation process via the readdition of the reactant gases to the reactor at any desired conventional temperature and pressure and continuing the same hydroformylation using said organic reagent treated reaction medium. Of course it is not necessary to stop the continuous hydroformylation process at all if such is not desired. For example yet another preferred aspect and benefit of this invention comprises treating all or part of the liquid catalyst containing recycle medium of a such a continuous hydroformylation process with an appropriate organic reagent and returning the thus treated catalyst containing recycle medium to the reaction medium in the reactor of the continuous hydroformylation process. Such may be accomplished by any suitable method, e.g., drawing off a part of the recycle medium to an appropriate container treating same and returning the treated medium, without any need for stopping or shutting down the continuous hydroformylation. Of course likewise a portion of the hydroformylation reation medium itself may be withdrawn from the reactor, and also so treated and returned to the reactor in the same fashion, if desired, without stopping or shutting down the continuous hydroformylation.

Further in addition to being readily returnable to the reaction medium of the same hydroformylation process from whence the partially deactivated rhodium - tertiary non-ionic organophosphine complex catalyst may be derived, if desired the organic reagent treated rhodium - tertiary non-ionic organophosphine complex product of this invention may be useful as the catalytic starting material or as a catalytic booster for any different conventional hydroformylation process if desired.

The following examples are illustrative of the present invention and are not to be regarded as limitative. It is to be understood that all parts, percentages and proportions referred to herein and in the appended claims are by weight unless otherwise indicated. Rhodium concentrations were determined using conventional atomic absorption spectroscopy (AAS). Moreover, the sodium salt of 3-(diphenylphosphino) benzene sulfonic acid may be represented has having the formula

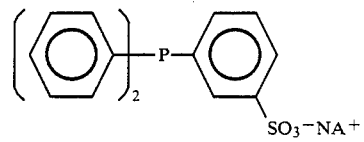

EXAMPLES 1 TO 15

This example illustrates increasing the amount of rhodium capable of being extracted into an aqueous solution of a sodium salt of 3-(diphenylphosphino) benzene sulfonic acid (TPPMS-Na) from an organic solution of a partially deactivated rhodium - triphenylphosphine complex hydroformylation catalyst composition that had been employed in a non-aqueous hydroformylation process directed to producing butyraldehyde by hydroformylating propylene and whose catalytic activity activity had declined from 100% active to about 85 percent of fresh catalyst.

Each experiment was conducted in essentially the same manner, the treatments being carried out in standard laboratory glassware and under an inert nitrogen atmosphere.

The procedure employed consisted of adding various amounts of the chemical reagents reported in the table below to individual 25 gram samples of said rhodium - triphenylphosphine complex catalyst composition consisting essentially of about 12 weight percent triphenylphosphine (TPP) ligand and about 272 ppm rhodium, calculated as rhodium metal, the remainder being essentially butyraldehyde product (about 75–80 weight percent) and hydroformylation by-products. About 25 grams of dioctylphthalate (DOP) was also added to each treated catalyst solution mixture to facilitate stripping of the butyraldehyde and other lights, and to allow for a more consistent continuous single pass reactor operation. Each solution mixture was then warmed to about 60° C. for about 4 hours and essentially all of the butyraldehye lights was nitrogen stripped from the solution. Each solution was then added to a single pass glass reactor and employed in a continuous single pass hydroformylation process directed to hydroformylating propylene (at about 100° C. using a gaseous mixture of about 100 psig. hydrogen, about 18 psig. carbon monoxide and about 23 psig. propylene) for from about 16 to about 28 hours. The catalyst solutions were then discharged from the glass reactor and the extractability of rhodium therefrom into an aqueous solution containing 10 weight percent of said TPPMS-Na ligand determined by the following procedure. In each example a 10 gram sample of each said discharged organic catalyst solution was mixed with 15 gram samples of said aqueous solution at room temperature for about 3 hours. The phases were allowed to separate and each was recovered and the amount of rhodium remaining in the organic phase measured and compared with that amount of rhodium in the 10 gram sample employed for said extraction. The results of each experiment as compared to the rhodium extractability from a fresh catalyst solution and the initial partially deactivated catalyst solution are given in the following Table 1.

lation process directed to producing butyraldehyde by hydroformylating propylene and whose catalytic activity activity had declined from 100% active to about 35 percent of fresh catalyst.

Each experiment was conducted in essentially the same manner, the treatments being carried out in standard laboratory glassware and under an inert nitrogen atmosphere.

The procedure employed consisted of adding various amounts of the chemical reagents reported in the table below to individual 25 gram samples of said rhodium - triphenylphosphine complex catalyst composition consisting essentially of about 12 weight percent triphenylphosphine (TPP) ligand and about 750 ppm rhodium, calculated as rhodium metal, the remainder being essentially butyraldehyde product (about 75–80 weight percent) and hydroformylation by-products. Each solution mixture was then warmed to temperature for the stated period of time given in the table below, and the extractability of rhodium therefrom into an aqueous solution containing 5 weight percent of said TPPMS-Na ligand determined by the following procedure. In each example a 50 gram sample of each organic solution of said rhodium - TPP complex catalyst composition (a 200 gram sample was used in Example 19 and a 20 gram sample was used in Example 20) was mixed with 10 gram samples (25 gram samples in Example 16, 17 and 19 and a 12 gram sample in Example 20) of said aqueous solution at 50° C. for thirty minutes. The phases were allowed to separate and each was recovered. Each extraction procedure was then repeated on each obtained organic phase and then sequentially repeated for a third time on the second obtained organic phase ( the same sequential extraction procedure being carried out a total

TABLE 1

| Ex. No. | Reagent | Reagent/ Rhodium[a] | Rhodium (ppm) Before[b] | Rhodium (ppm) After[c] | Rhodium % Recovery[e] |
|---|---|---|---|---|---|
| 1 | None | (Fresh Catalyst) | 272 | 3 | 99 |
| 2 | None | (Spent Catalyst)[d] | 272 | 41 | 85 |
| 3 | Allyl Chloride | 4.98 | 214 | 6 | 97 |
| 4 | Propargyl Benzene Sulfonate | 10.04 | 200 | 9 | 96 |
| 5 | Propargyl Chloride | 10.13 | 225 | 11 | 95 |
| 6 | Furfuryl Acetate | 10.75 | 222 | 10 | 96 |
| 7 | Allyl Methacrylate | 10.00 | 203 | 6 | 97 |
| 8 | Benzyl Acetate | 9.92 | 224 | 6 | 97 |
| 9 | Cyclohexene Oxide | 10.04 | 211 | 5 | 98 |
| 10 | Cyclopentene Oxide | 10.00 | 202 | 3 | 99 |
| 11 | Diketene | 10.08 | 203 | 5 | 98 |
| 12 | Propargyl Triphenylphosphonium Bromide | 9.89 | 209 | 11 | 95 |
| 13 | Allyl Trifluoroacetate | 9.82 | 255 | 21 | 92 |
| 14 | Ethyl Propiolate | 10.0 | 212 | 5 | 98 |
| 15 | Propargyl Alcohol | 10.0 | 222 | 5 | 98 |

[a]Reagent to Rhodium Molar Ratio.
[b]Amount of rhodium, parts per million, before extraction in organic solution starting material.
[c]Amount of rhodium, parts per million, after extraction remaining in the separated organic phase.
[d]Initial partially deactivated untreated catalyst solution starting material.
[e]Rhodium recovery extraction efficiency.

EXAMPLES 16 TO 25

This example illustrates increasing the amount of rhodium capable of being extracted into an aqueous solution of a sodium salt of 3-(diphenylphosphino) benzene sulfonic acid (TPPMS-Na) from an organic solution of a partially deactivated rhodium - triphenylphosphine complex hydroformylation catalyst composition that had been employed in a non-aqueous hydroformyof five times in Example 19). The amount of rhodium remaining in the final obtained organic phase of each example was then measured and compared with that amount of rhodium in the initial sample of the organic solution starting material. The results of each experiment as compared to rhodium extractable from the initial partially deactivated catalyst solution are given in the following TABLE 2.

TABLE 2

| Ex. No. | Reagent | Reagent Amount (Grams) | Time (Hours) | Temp. (°C.) | Rhodium (ppm) Before[a] | Rhodium (ppm) After[b] | Rhodium % Recovery[c] |
|---|---|---|---|---|---|---|---|
| 16 | (Spent Catalyst[d]) | None | 0 | 0 | 750 | 482 | 36 |
| 17 | Allyl Chloride | 0.2 | 1 | 25 | 750 | 343 | 54 |
| 18 | Allyl Chloride | 0.5 | 16 | 100 | 750 | 213 | 72 |
| 19 | Allyl Chloride | 2.0 | 24 | 100 | 750 | 125 | 83 |
| 20 | Benzyl Bromide | 0.47 | 24 | 100 | 750 | 122 | 84 |
| 21 | Allyl Chloride | 0.13 | 4 | 60 | 750 | 115 | 85 |
| 22 | Allyl Acetate | 0.17 | 4 | 60 | 750 | 210 | 72 |
| 23 | Allyl Bromide | 0.21 | 4 | 60 | 750 | 105 | 86 |
| 24 | Allyl Butyrate | 0.22 | 4 | 60 | 750 | 240 | 68 |
| 25 | Allyl Iodide | 0.29 | 4 | 60 | 750 | 207 | 72 |

[a]Amount of rhodium, parts per million, before extraction in organic solution starting material.
[b]Amount of rhodium, parts per million after extraction remaining in final obtained separated organic phase.
[c]Rhodium recovery extraction efficiency.
[d]Initial partially deactivated untreated catalyst solution starting material.

EXAMPLES 26 TO 30

Each of the following Examples 26 to 30 employed a 25 sample of a catalyst solution derived from a continuous non-aqueous hydroformylation process directed to producing butyraldehyde from propylene using a rhodium - TPP complex catalyst, which had been operated for a sufficient period of time to cause intrinsic deactivation of the catalyst to about 42% of a fresh catalyst. The partially deactivated catalyst solutions employed contained about 450 pmm rhodium, calculated as rhodium metal, about 12 wt.% triphenylphosphine (TPP) and about 14 wt.% butyraldehyde, the remainder being hydroformylation by-products, e.g., aldehyde condensation by products.

Each untreated catalyst solution (20 gram samples) was charged to a continuously operating single pass hydroformylation reactor. A mixture of carbon monoxide, hydrogen, propylene and nitrogen was fed to the reacting system. The reactor was heated to 100° C. and a steady state mixture of reactant gases (i.e., syn gas and propylene) was obtained in the system (carbon monoxide about 18 psig; hydrogen about 95 psig; propylene about 23 psig). Total reaction pressure was about 160 psig. The butyraldehyde production rates, in gram moles per liter per hour, were determined by monitoring the flow rate and composition of off-gases from the reactor.

Once stable production rate had been achieved (note Table 3 below) the reacting gases were valved off to the reactor and the prescribed amount of organic reagent of Table 4 below added to each solution contained in the reactor and in the absence of said reactant gases. The contents of the reactor were then held at temperature under 160 psig. nitrogen for the period of time given in Table 4 below. (In Example 27, 100 equivalents of the organic reagent based on the total rhodium content was added to the catalyst solution every hour for 5 hours.) The reacting gases i.e., syn gas and propylene, were then re-introduced to the reactor establishing the previously achieved reaction conditions. Upon re-introduction of the gases each reaction was continued until a stable aldehyde production rate was re-achieved, within 5 to 16 hours. Each reaction solution was then removed from the reactor and the extractability of rhodium therefrom into an aqueous solution containing 5 weight percent of the sodium salt of 3-(diphenylphosphino) benzene sulfonic acid (TPPMS-Na) ligand determined by the following procedure. In each example a 15 gram sample of each organic solution of said organic reagent treated rhodium - TPP complex catalyst composition was mixed with 7.5 gram samples of said aqueous solution at 50° C. for thirty minutes. The phases were allowed to separate and each was recovered. The same extraction procedure was repeated on each obtained organic phase and then sequentially repeated for a third time on the second obtained organic phase. The amount of rhodium remaining in the final obtained organic phase of each example as well as in each aqueous phase was measured and compared with that amount of rhodium in the initial sample of the organic solution starting material. The results of each experiment as compared to rhodium extractable from a sample of the initial partially deactivated catalyst solution by the same procedure are given in the following TABLE 5.

TABLE 3

| EX No. | Stable Hydroformylation Rate[a] | % of Fresh Catalyst | Time (Hours) |
|---|---|---|---|
| 26 | 1.42 | 42 | 83 |
| 27 | 1.25 | 40 | 42 |
| 28 | 1.27 | 39 | 80 |
| 29 | 1.48 | 35 | 86 |
| 30 | — | — | — |

[a]Butyraldehyde production in gram, moles per liter per hour.

TABLE 4

| Ex. No. | Organic Reagent | Reagent (Grams) | Reagent/ Rhodium[a] | Treatment Temp. (°C.) | Treatment Time (Hours) |
|---|---|---|---|---|---|
| 26 | Propargyl Cyanoacetate | 0.38 | 35 | 70 | 16 |
| 27 | Propargyl Acetate | 4.34 | 500 | 100 | ? |
| 28 | Propargyl Acetate | 0.86 | 100 | 100 | 16 |
| 29 | Propargyl Propionate | 0.99 | 100 | 100 | 21 |
| 30 | Spent Catalyst[b] | None | — | — | — |

[a]Reagent to rhodium mole ratio.
[b]Initial partially deactivated untreated catalyst solution starting material.

TABLE 5

| Ex. No. | Rh (ppm) Before[a] | Ph (ppm) 1st Aqueous Phase[b] | Rh (ppm) 2nd Aqueous Phase[c] | Rh (ppm) 3rd Aqueous Phase[d] | Rh (ppm) After[e] | Rh Percent Recovered[f] |
|---|---|---|---|---|---|---|
| 26 | 481 | 316 | 205 | 110 | 184 | 62 |
| 27 | 422 | 593 | 93 | 31 | 79 | 81 |
| 28 | 508 | 581 | 145 | 44 | 109 | 79 |
| 29 | 442 | 548 | 130 | 38 | 70 | 84 |
| 30 | 456 | 158 | 101 | 53 | 284 | 38 |

[a] Amount of rhodium, parts per million, before extraction in organic solution starting material.
[b] Amount of rhodium, parts per million, in first extracted aqueous phase.
[c] Amount of rhodium, parts per million, in second extracted aqueous phase.
[d] Amount of rhodium, parts per million, the third extracted aqueous phase.
[e] Amount of rhodium, parts per million, after three extractions remaining in final obtained separated organic phase.
[f] Rhodium recovery extraction efficiency.

EXAMPLES 31 TO 32

Two 50 gram samples of a concentrated catalyst solution derived from a continuous non-aqueous hydroformylation process directed to producing butraldehyde from propylene using a rhodium - TPP complex catalyst, which had been operated for a sufficient period of time to cause serve intrinsic deactivation of the catalyst to about 42% of a fresh catalyst, and containing about 11,898 ppm rhodium, calculated as rhodium metal and a minor amount of triphenylphosphine (TPP), the remainder consisting essentially of triphenylphosphine oxide and high boiling hydroformylation by-products, e.g., aldehyde pentamers were obtained via the procedure described in U.S. Pat No. 4,297,239.

Each experiment was conducted in essentially the same manner, the treatments being carried out in standard laboratory glassware and under an inert nitrogen atmosphere.

About 0.7 grams of allyl chloride was added to and mixed with one said 50 grams sample solutions and the solution warmed to about 80° C. for 48 hours (Examples 31). The other 50 gram sample solution was left untreated (Example 32).

The extractability of rhodium from said 50 gram samples was determined by mixing them with 25 gram samples of an aqueous solution of 10 percent by weight of the sodium salt of 3-(diphenylphosphino)-benzene sulfonic acid (TPPMS-Na) ligand at 50° C. for about thirty minutes. The phases were allowed to separate and each was recovered. The same extraction procedure was repeated on each obtained organic phase and then sequentially repeated for a third time on the second obtained organic phase. The amount of rhodium remaining in the final obtained organic phase of each example was then measured and compared with the amount of rhodium in the initial sample of the organic solution starting material. The results of each experiment are given in the following TABLE 6.

TABLE 6

| Ex. No. | Organic Reagent | Rh (ppm) Before[a] | Rh (ppm) After[b] | Rh (%) Recovery[c] |
|---|---|---|---|---|
| 31 | Allyl Chloride | 11,898 | 2,763 | 77 |
| 32 | None | 11,898 | 5,723 | 52 |

[a] Amount of rhodium, parts per million, before extraction, in the organic solution starting material.
[b] Amount of rhodium, parts per million, after extraction remaining in final obtained separated organic phase.
[c] Rhodium recovery extraction efficiency.

Various modifications and variations of this invention will be obvious to a worker skilled in the art and it is to be understood that such modifications and variations are to be included within the purview of this application and the spirit and scope of the appended claims.

What is claimed is:

1. A process for increasing the amount of rhodium capable of being extracted into an aqueous solution containing an ionic organophosphine ligand, which rhodium is present in an organic solution containing a partially deactivated rhodium - tertiary non-ionic organophosphine complex catalyst, said process comprising mixing under non-hydroformylation conditions, said organic solution with an organic reagent selected from the group consisting of (a) alkyne compounds having the formula $R-C\equiv C-CH_2-X$, (b) alkene compounds having the formula $(R^1)(R^2)C=C(R^3)-CH_2-X$, (c) diketene, (d) methyl halides, (e) methyl sulfonates, (f) propiolate compounds having the formula $HC\equiv C-C(O)OR^{14}$, and (g) oxide compounds having the formula

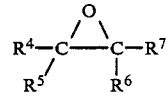

wherein X represents a radical selected from the group consisting of halogen atoms, a hydroxyl radical, a carboxylate radical of the formula $-OC(O)R^8$, a sulfonate radical of the formula $-OSO_2R^8$ a phosphonium radical of the formula $[-P^{30}(R^8)_3][Y-]$; wherein $R^8$ in the above formulae for X, each individually represent a monovalent hydrocarbon radical having from 1 to 18 carbon atoms selected from the group consisting of alkyl, aryl, aralkyl, alkaryl and cycloalkyl radicals and wherein Y represents an acid anion; and wherein each R, $R^1$, $R^2$, $R^3$, $R^4$, $R^5$, $R^6$, $R^7$, and $R^{14}$ radical individually represents hydrogen or a monovalent hydrocarbon radical having from 1 to 18 carbon atoms selected from the group consisting of alkyl, aryl, alkaryl, aralkyl and cycloalkyl radicals; with the following provisos: that $R^8$ in the above carboxylate formula can also be hydrogen; that $R^2$ and $R^3$ in the above formula for the alkene compounds can also be bonded together to form a five or six membered heterocyclic ring or monocyclic hydrocarbon ring along with the $C=C$ group shown in said formula; and wherein any two of said $R^4$, $R^5$, $R^6$ and $R^7$ groups in the above formula for the oxides can be bonded together to form a five or six membered monocyclic hydrocarbon ring along with the C—C group shown in said formula; to obtain an organic solution of an organic reagent treated solubilized rhodium - tertiary non-ionic organophosphine complex product that contains more rhodium correspondingly capable of being extracted into an aqueous solution containing an ionic organophosphine ligand than contained in the organic solution starting material of this process.

2. A process as defined in claim 1, wherein the organic reagent is an alkyne compound having the above defined formula and wherein X represents a radical selected from the group consisting of halogen, a hydroxyl radical, and a carboxylate radical having the above formula.

3. A process as defined in claim 2, wherein R represents hydrogen.

4. A process as defined in claim 3, wherein X represents a carboxylate radical.

5. A process as defined in claim 3, wherein X represents a halogen atom.

6. A process as defined in claim 3, wherein X represents a hydroxy radical.

7. A process as defined in claim 3, wherein the organic reagent is selected from the group consisting of propargyl acetate, propargyl cyanoacetate, propargyl propionate and propargyl chloride, and propargyl alcohol.

8. A process a defined in claim 2, wherein said partially deactivated rhodium - tertiary non-ionic organophosphine complex catalyst is a hydroformylation catalyst derived from a process involving the hydroformylation of an alpha olefin.

9. A process as defined in claim 8, wherein the tertiary non-ionic organophosphine is triphenylphosphine.

10. A process as defined in claim 1, wherein the organic reagent is an alkene compound having the above formula and wherein X represents a radical selected from the group consisting of halogen, a carboxylate radical having the above formula, and a sulfonate radical having the above formula.

11. A process as defined in claim 10, wherein $R^1$, $R^2$ and $R^3$ each represent hydrogen.

12. A process as defined in claim 11, wherein X represents a halogen atom.

13. A process as defined in claim 11, wherein X represents a carboxylate radical.

14. A process as defined in claim 10, wherein said partially deactivated rhodium - tertiary non-ionic organophosphine complex catalyst is a hydroformylation catalyst derived from a process involving the hydroformylation of an alpha olefin.

15. A process as defined in claim 14, wherein the tertiary non-ionic organophosphine is triphenylphosphine.

16. A process as defined in claim 8, wherein the organic reagent is selected from the group consisting of propargyl acetate, propargyl chloride, propargyl cyanoacetate, and propargyl propionate, and propargyl alcohol.

17. A process as defined in claim 10, wherein the organic reagent is selected from the group consisting of allyl acetate, allyl propionate, allyl butyrate, allyl methacrylate, furfuryl acetate, allyl trifluroacetate, benzyl acetate, allyl chloride, allyl bromide, allyl iodide, allyl benzene sulfonate, allyl cyanoacetate, allyl triphenylphosphonium bromide and benzyl bromide.

18. A process as defined in claim 14, wherein the organic reagent is an alkene halide.

19. A process as defined in claim 1, wherein the organic reagent is a propiolate compound.

20. A process as defined in claim 19, wherein $R^{14}$ represents a phenyl radical or an alkyl radical.

21. A process as defined in claim 20 wherein the organic reagent is ethyl propiolate.

22. A process as defined in claim 1, wherein the organic reagent is a methyl halide.

23. A process as defined in claim 1, wherein the organic reagent is a methyl sulfonate.

24. A process as defined in claim 1, wherein the organic reagent is an oxide compound.

25. A process as defined in claim 1, wherein the organic reagent is diketene.

26. A process as defined in claim 1, wherein said mixing is conducted at a temperature in the range of from about 10° C. to about 180° C. and wherein the amount of organic reagant employed is in the range from about 0.1 to about 1000 moles per mole of rhodium, calculated as rhodium metal, in the organic solution starting material.

27. A process as defined in claim 26, wherein at least one mole of the organic reagent per mole of said rhodium is employed.

* * * * *

UNITED STATES PATENT AND TRADEMARK OFFICE
CERTIFICATE OF CORRECTION

PATENT NO.   :  4,929,767
DATED        :  May 29, 1990
INVENTOR(S)  :  D. J. Miller et al.

It is certified that error appears in the above-identified patent and that said Letters Patent is hereby corrected as shown below:

Column 7, line 27, replace "orqano" with -- organo --.

Column 14, line 1, the formula should read -- $HC\equiv C-C(O)OR^{14}$ --.

Column 19, line 53, the numeral "(7)" should read -- (2) --.

Column 22, line 42, "adjiv" should read --ajuv--.

Column 26, line 68, after the phrase "of the" should read the phrase -- above formulae -- should be inserted.

Column 38, line 28, the formula "$R-C=C-CH_2-X$" should read -- $R-C\equiv C-CH_2-X$ --.

Column 38, line 32, "$HC=C-C(O)OR^{14}$" should read -- $HC\equiv C-C(O)OR^{14}$ --.

Column 38, line 44, delete the formula "$[-P^{30}(R^8)_3]\,[Y-]$" and substitute therefore the formula -- $[-P^+(R^8)_3]\,[Y-]$ --.

Signed and Sealed this

Fourteenth Day of January, 1992

*Attest:*

*Attesting Officer*

HARRY F. MANBECK, JR.

*Commissioner of Patents and Trademarks*